US012697309B2

(12) United States Patent
Karve et al.

(10) Patent No.: US 12,697,309 B2
(45) Date of Patent: Aug. 4, 2026

(54) MRNA-LOADED LIPID NANOPARTICLES AND PROCESSES OF MAKING THE SAME

(71) Applicant: Translate Bio, Inc., Lexington, MA (US)

(72) Inventors: Shrirang Karve, Lexington, MA (US); Ashish Sarode, Lexington, MA (US); Frank DeRosa, Lexington, MA (US)

(73) Assignee: Translate Bio, Inc., Waltham, MA (US)

( * ) Notice: Subject to any disclaimer, the term of this patent is extended or adjusted under 35 U.S.C. 154(b) by 1215 days.

(21) Appl. No.: 17/625,507

(22) PCT Filed: Jul. 8, 2020

(86) PCT No.: PCT/US2020/041122

§ 371 (c)(1),
(2) Date: Jan. 7, 2022

(87) PCT Pub. No.: WO2021/007278

PCT Pub. Date: Jan. 14, 2021

(65) Prior Publication Data

US 2023/0181483 A1 Jun. 15, 2023

Related U.S. Application Data

(60) Provisional application No. 62/871,513, filed on Jul. 8, 2019.

(51) Int. Cl.

| | |
|---|---|
| ***A61K 9/51*** | (2006.01) |
| ***A61K 9/00*** | (2006.01) |
| ***A61K 9/127*** | (2025.01) |
| ***A61K 9/1272*** | (2025.01) |
| ***A61K 38/00*** | (2006.01) |
| ***A61K 47/54*** | (2017.01) |
| ***A61K 47/69*** | (2017.01) |
| ***C12N 15/88*** | (2006.01) |

(52) U.S. Cl.

CPC .......... *A61K 9/5192* (2013.01); *A61K 9/0019* (2013.01); *A61K 9/1272* (2013.01); *A61K 9/5123* (2013.01); *A61K 47/544* (2017.08); *A61K 47/6929* (2017.08); *A61K 38/00* (2013.01); *C12N 15/88* (2013.01)

(58) Field of Classification Search

None

See application file for complete search history.

(56) References Cited

U.S. PATENT DOCUMENTS

| | | | |
|---|---|---|---|
| 4,373,071 | A | 2/1983 | Itakura |
| 4,401,796 | A | 8/1983 | Itakura |
| 4,415,732 | A | 11/1983 | Caruthers et al. |
| 4,458,066 | A | 7/1984 | Caruthers et al. |
| 4,500,707 | A | 2/1985 | Caruthers et al. |
| 4,668,777 | A | 5/1987 | Caruthers et al. |
| 4,897,355 | A | 1/1990 | Eppstein et al. |
| 4,973,679 | A | 11/1990 | Caruthers et al. |
| 5,047,524 | A | 9/1991 | Andrus et al. |
| 5,132,418 | A | 7/1992 | Caruthers et al. |
| 5,153,319 | A | 10/1992 | Caruthers et al. |
| 5,171,678 | A | 12/1992 | Behr et al. |
| 5,262,530 | A | 11/1993 | Andrus et al. |
| 5,334,761 | A | 8/1994 | Gebeyehu et al. |
| 5,700,642 | A | 12/1997 | Monforte et al. |
| 5,744,335 | A | 4/1998 | Wolff et al. |
| 5,885,613 | A | 3/1999 | Holland et al. |
| 9,668,980 | B2 | 6/2017 | Derosa et al. |
| 10,201,618 | B2 | 2/2019 | Anderson et al. |
| 11,547,666 | B2 | 1/2023 | Zhang et al. |
| 11,964,051 | B2 | 4/2024 | Derosa et al. |
| 12,076,439 | B2 | 9/2024 | Zhang et al. |
| 12,144,871 | B2 | 11/2024 | Karve et al. |
| 12,240,824 | B2 | 3/2025 | Zhang et al. |
| 2011/0244026 | A1 | 10/2011 | Guild et al. |
| 2016/0038432 | A1 | 2/2016 | Derosa et al. |
| 2018/0125989 | A1 | 5/2018 | Derosa et al. |
| 2018/0153822 | A1 | 6/2018 | Karve et al. |
| 2023/0071228 | A1 | 3/2023 | Zhang et al. |
| 2024/0342269 | A1 | 10/2024 | Dias et al. |

FOREIGN PATENT DOCUMENTS

| | | | |
|---|---|---|---|
| EP | 3315125 | A1 | 5/2018 |
| WO | WO 2005/121348 | A1 | 12/2005 |
| WO | WO 2010/042877 | A1 | 4/2010 |
| WO | WO 2010/053572 | A2 | 5/2010 |
| WO | WO 2010/144740 | A1 | 12/2010 |
| WO | WO 2012/170889 | A1 | 12/2012 |
| WO | WO 2013/063468 | A1 | 5/2013 |
| WO | WO 2013/149140 | A1 | 10/2013 |

(Continued)

OTHER PUBLICATIONS

Mochizuki, et al. (2013) "The role of helper lipid dioleoylphosphatidylethanolamine (DOPE) for DNA transfection cooperating with a cationic lipid bearing ethylenediamine", Biochimica et Biophysica Acta (BBA)—Biomembranes, 1828(2): 412-418. (Year: 2013).*

Kim, et al. (2015) "DOPTAP/DOPE ratio and cell type determine transfection efficiency with DOTAP-liposomes", Biochimica et Biophysica Acta, 1848: 1996-2001. (Year: 2015).*

International Preliminary Report on Patentability for PCT Application No. PCT/US20/41122, 6 pages, dated Jan. 11, 2022.

International Search Report and Written Opinion for PCT Application No. PCT/US20/41122, 12 pages, dated Oct. 2, 2020.

Behr et al., "Efficient gene transfer into mammalian primary endocrine cells with lipopolyamine-coated DNA," Proc Natl Acad Sci U S A. (1989) 86(18):6982-6.

Berge et al., "Pharmaceutical salts," J Pharm Sci. (1977) 66(1):1-19.

Budker et al., "Protein/amphipathic polyamine complexes enable highly efficient transfection with minimal toxicity," Biotechniques. (1997) 23(1):139, 142-7.

(Continued)

*Primary Examiner* — Robert M Kelly

(74) *Attorney, Agent, or Firm* — Steptoe LLP; Z. Ying Li; David Caianiello

(57) ABSTRACT

The present invention provides an improved lipid nanoparticle formulation encapsulating mRNA comprising DEPE as a helper lipid.

18 Claims, 2 Drawing Sheets

(56) References Cited

FOREIGN PATENT DOCUMENTS

| | | | |
|---|---|---|---|
| WO | WO 2015/095340 | A1 | 6/2015 |
| WO | WO 2015/184256 | A2 | 12/2015 |
| WO | WO 2015/199952 | A1 | 12/2015 |
| WO | WO 2016/004202 | A1 | 1/2016 |
| WO | WO 2016/118724 | A1 | 7/2016 |
| WO | WO 2016/118725 | A1 | 7/2016 |
| WO | WO 2016/205691 | A1 | 12/2016 |
| WO | WO 2017/004143 | A1 | 1/2017 |
| WO | WO 2017/049245 | A2 | 3/2017 |
| WO | WO 2017/075531 | A1 | 5/2017 |
| WO | WO 2017/117528 | A1 | 7/2017 |
| WO | WO 2017/173054 | A1 | 10/2017 |
| WO | WO 2018/089790 | A1 | 5/2018 |
| WO | WO 2018/089801 | A1 | 5/2018 |
| WO | WO 2018/165257 | A1 | 9/2018 |
| WO | WO 2018/231709 | A1 | 12/2018 |
| WO | WO 2020/011953 | A1 | 1/2020 |
| WO | WO 2020/097384 | A1 | 5/2020 |
| WO | WO 2020/097511 | A2 | 5/2020 |
| WO | WO 2021/007278 | A1 | 1/2021 |

OTHER PUBLICATIONS

Fechter et al., "Recognition of mRNA cap structures by viral and cellular proteins" J Gen Virol. (2005) 86(Pt 5):1239-49.

Gao et al., "A novel cationic liposome reagent for efficient transfection of mammalian cells," Biochem Biophys Res Commun. (1991) 179(1):280-5.

Heyes et al., "Cationic lipid saturation influences intracellular delivery of encapsulated nucleic acids," J Control Release. (2005) 107(2):276-87.

Klibanov et al., "Amphipathic polyethyleneglycols effectively prolong the circulation time of liposomes," FEBS Lett. (1990) 268 (1): 235-7.

McClellan et al., "Genetic heterogeneity in human disease," Cell. (2010) 141(2):210-7.

Morrissey et al., "Potent and persistent in vivo anti-HBV activity of chemically modified siRNAs," Nat Biotechnol. (2005) 23(8):1002-7.

Semple et al., "Rational design of cationic lipids for siRNA delivery," Nat Biotechnol. (2010) 28(2):172-6.

Whitehead et al., "Degradable lipid nanoparticles with predictable in vivo siRNA delivery activity," Nat Commun. (2014) 5:4277.

* cited by examiner

MRNA-LOADED LIPID NANOPARTICLES AND PROCESSES OF MAKING THE SAME

CROSS-REFERENCE TO RELATED APPLICATIONS

The present application is a 35 U.S.C. § 371 National Stage Application of International Application No. PCT/US20/41122, filed on Jul. 8, 2020, which claims priority to U.S. Provisional Application Ser. No. 62/871,513 filed Jul. 8, 2019, the disclosures of which are hereby incorporated by reference.

FIELD OF INVENTION

The invention relates to lipid mediated mRNA delivery; and the lipid compounds and compositions comprising such compounds thereof. Particularly, this invention relates to methods and uses of such compounds and compositions, and to processes for making such compounds and compositions.

BACKGROUND OF THE INVENTION

Messenger RNA therapy (MRT) is becoming an increasingly important approach for the treatment or prevention of a variety of diseases. MRT involves administration of messenger RNA (mRNA) to a subject in need of the therapy in order to provide for the production of the protein encoded by the mRNA within the subject's body. Lipid nanoparticles can be used to encapsulate mRNA for efficient in vivo delivery of mRNA.

Much effort has been put on identifying novel methods and compositions that can enhance intracellular delivery and/or expression of mRNA using lipid nanoparticles, which can be adapted to a scalable and cost-effective manufacturing process. At the same time, it is important that any such enhancements to intracellular delivery and/or expression of mRNA also maintain or improve upon the safety and tolerability of the compositions associated with lipid mediated mRNA delivery.

Multi-component lipid nanoparticles comprising one or more cationic lipids, one or more PEG-modified lipids and one or more helper lipids encapsulating an mRNA have been found to be particularly effective for achieving delivery and expression of mRNA in vivo. A particular focus of recent research has been on the discovery of new cationic lipids for mRNA delivery. The other components of multi-component lipid nanoparticles have received little to no attention. There is a continuing need to improve upon lipid nanoparticle delivery of mRNA to achieve intracellular delivery and/or expression of mRNA. At the same time it is desirable that new lipid nanoparticle formulations maintain or improve upon the safety and tolerability.

SUMMARY OF THE INVENTION

The inventors have surprisingly found that delivery and/or expression of mRNA in vivo can be improved dramatically by optimizing the helper lipid component of multicomponent liposomes encapsulating the mRNA. In particular, the present invention is based on the discovery that the presence of 1,2-Dierucoyl-sn-glycero-3-phosphoethanolamine (DEPE) as a helper lipid in mRNA-encapsulating lipid nanoparticle formulations comprising one or more cationic lipids, one or more PEG-modified lipids and one or more helper lipids can increase delivery and/or expression of mRNA in vivo by more than two-fold relative to conventional liposomes comprising dioleoylphosphatidylethanolamine (DOPE) as one of the helper lipids. DEPE-containing lipid nanoparticles were comparable DOPE-containing lipid nanoparticles in terms of safety and tolerability (as assessed by liver toxicity markers such as ALT and AST).

Accordingly, it is an aspect of the invention to provide a lipid nanoparticle for the delivery of mRNA to a subject in need thereof, wherein the lipid nanoparticle comprises one or more cationic lipids, one or more PEG-modified lipids and one or more helper lipids encapsulating the mRNA, wherein the one or more helper lipids comprises 1,2-Dierucoyl-sn-glycero-3-phosphoethanolamine (DEPE). The DEPE in the lipid nanoparticle provides for the enhanced expression of the mRNA when administered to a subject.

In embodiments of the invention, DEPE 1,2-Dierucoyl-sn-glycero-3-phosphoethanolamine (DEPE) is structurally represented by the following structure:

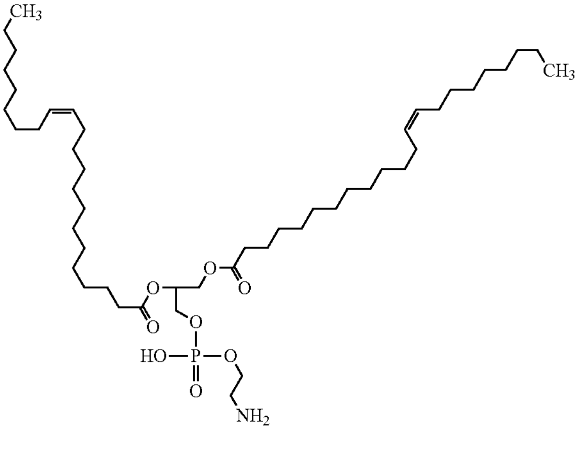 [SMILES: CCCCCCCC/C=C\CCCCCCCCCCCC(=O)OCC(COP(=O)(O)OCCN)OC(=O)CCCCCCCCCCC/C=C\CCCCCCCC]

or by the following structure.

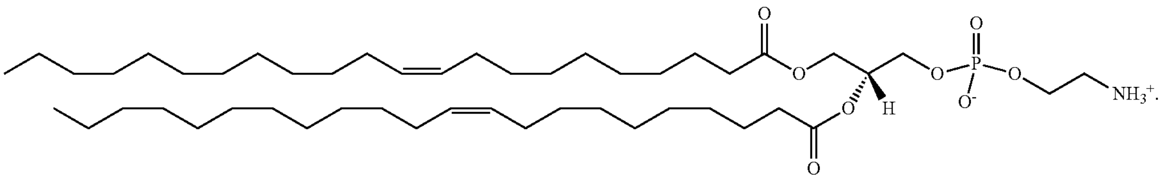

In embodiments of the invention, the enhanced expression of the mRNA is more as compared to expression of the same mRNA from a second lipid nanoparticle having the same lipid components and amounts except that it includes different one or more helper lipids and does not include DEPE. In certain embodiments, the enhanced expression is increased by two-fold or more relative to the second lipid nanoparticle. In some embodiments, the different one or more helper lipids in the second lipid nanoparticle comprises dioleoylphosphatidylethanolamine (DOPE), 1,2-Dilinoleoyl-sn-glycero-3-phosphoethanolamine (DLOPE), 1-palmitoyl-2-oleoyl-sn-glycero-3-phosphoethanolamine (POPE), and/or a combination thereof.

In certain embodiments, the DEPE in the lipid nanoparticle is present at a concentration of at least 0.5 molar percent of total lipids in the lipid nanoparticle, for example at a concentration of between 0.5 molar percent and 50 molar percent, in particular at a concentration of between 10 molar percent and 45 molar percent. More typically, the DEPE in the lipid nanoparticle is present at a concentration of between 25 molar present and 35 molar percent of total lipids in the lipid nanoparticle.

In certain embodiments, the one or more cationic lipids is or comprises cKK-E12.

In certain embodiments, the one or more cationic lipids is or comprises ICE (imidazole cholesterol ester).

In certain embodiments, the one or more cationic lipids is or comprise a cationic lipid of the following formula:

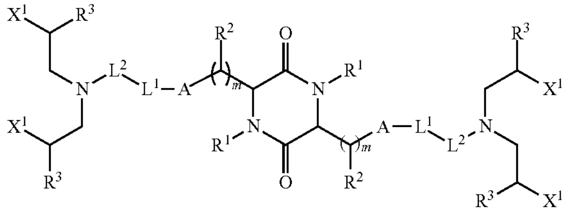

or a pharmaceutically acceptable salt thereof;

wherein each $R^1$ and $R^2$ is independently H or $C_1$-$C_6$ aliphatic; each m is independently an integer having a value of 1 to 4; each A is independently a covalent bond or arylene; each $L^1$ is independently an ester, thioester, disulfide, or anhydride group; each $L^2$ is independently $C_2$-$C_{10}$ aliphatic; each $X^1$ is independently H or OH; and each $R^3$ is independently $C_6$-$C_{20}$ aliphatic. In a specific embodiment, the one or more cationic lipids is or comprises the following compound:

(Compound 1)

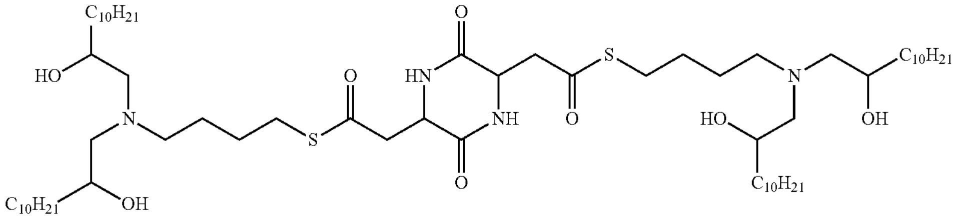

or a pharmaceutically acceptable salt thereof. In another specific embodiment, the one or more cationic lipids is or comprises the following compound:

(Compound 2)

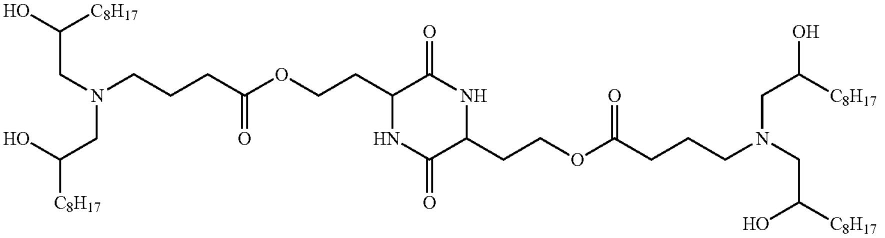

or a pharmaceutically acceptable salt thereof. In another specific embodiment, the one or more cationic lipids is or comprises the following compound:

(Compound 3)

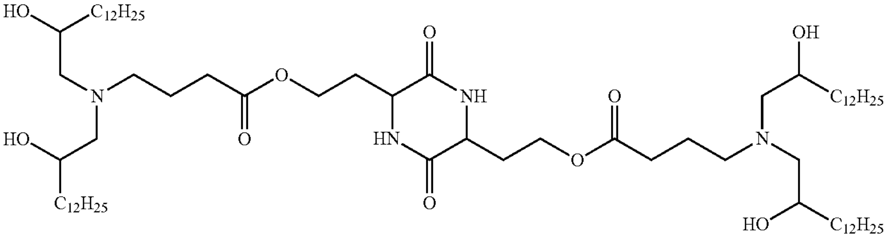

or a pharmaceutically acceptable salt thereof. In certain embodiments, the one or more PEG-modified lipids is or comprises a poly(ethylene) glycol chain of up to 5 kDa in length covalently attached to a lipid with alkyl chain(s) of $C_6$-$C_{20}$ length.

In some embodiments, the lipid nanoparticle that encapsulates mRNA and includes DEPE as a helper lipid also includes a cationic lipid that comprises alkyl chain(s) of $C_6$-$C_{20}$ length. In some embodiments, the cationic lipid comprises one to four alkyl chain(s) each of $C_8$-$C_{16}$ length. In some embodiments, the cationic lipid comprises one to four alkyl chain(s) each of $C_{10}$-$C_{16}$ length. In some embodiments, the cationic lipid comprises one to four alkyl chain(s) each f $C_{10}$-$C_{14}$ length. In some embodiments, the cationic lipid comprises one to four alkyl chain(s) each of $C_{10}$ length. In some embodiments, the cationic lipid comprises one to four alkyl chain(s) each of $C_{12}$ length. In some embodiments, the cationic lipid comprises one to four alkyl chain(s) each of $C_{16}$ length.

In some embodiments, the lipid nanoparticle that encapsulates mRNA and includes DEPE as a helper lipid also includes a cationic lipid that comprises one to four aliphatic chain(s) each of $C_6$-$C_{20}$ length. In some embodiments, the cationic lipid comprises one to four aliphatic chain(s) each of $C_8$-$C_{16}$ length. In some embodiments, the cationic lipid comprises one to four aliphatic chain(s) each of $C_{10}$-$C_{14}$ length. In some embodiments, the cationic lipid comprises one to four aliphatic chain(s) each of $C_{10}$ length. In some embodiments, the cationic lipid comprises one to four aliphatic chain(s) each of $C_{12}$ length. In some embodiments, the cationic lipid comprises aliphatic chain(s) each of $C_{16}$ length.

In some embodiments, the lipid nanoparticle that encapsulates mRNA and includes DEPE as a helper lipid also includes one or more cationic lipids that is or comprises a lipidoid. In some embodiments, the lipidoid comprises four aliphatic chains. In some embodiments, each of the four lipidoid aliphatic chains is independently $C_6$-$C_{20}$ in length. In some embodiments, each of the four lipidoid aliphatic chains is independently $C_8$-$C_{16}$ in length. In some embodiments, each of the four lipidoid aliphatic chains is independently $C_{10}$-$C_{14}$ in length. In some embodiments, each of the four lipidoid aliphatic chains is independently $C_{10}$ or $C_{12}$ in length. In some embodiments, all of the four lipidoid aliphatic chains are $C_6$ in length. In some embodiments, all of the four lipidoid aliphatic chains are $C_8$ in length. In some embodiments, all of the four lipidoid aliphatic chains are $C_{10}$ in length. In some embodiments, all of the four lipidoid aliphatic chains are $C_{12}$ in length. In some embodiments, all of the four lipidoid aliphatic chains are $C_{14}$ in length. In some embodiments, all of the four lipidoid aliphatic chains are $C_{16}$ in length. In some embodiments, all of the four lipidoid aliphatic chains are $C_{18}$ in length. In some embodiments, all of the four lipidoid aliphatic chains are $C_{20}$ in length. In some embodiments, at least two of the four lipidoid aliphatic chains are $C_6$ in length. In some embodiments, at least two of the four lipidoid aliphatic chains are $C_8$ in length. In some embodiments, at least two of the four lipidoid aliphatic chains are $C_{10}$ in length. In some embodiments, at least two of the four lipidoid aliphatic chains are $C_{12}$ in length. In some embodiments, at least two of the four lipidoid aliphatic chains are $C_{14}$ in length. In some embodiments, at least two of the four lipidoid aliphatic chains are $C_{16}$ in length. In some embodiments, at least two of the four lipidoid aliphatic chains are $C_{18}$ in length. In some embodiments, at least two of the four lipidoid aliphatic chains are $C_{20}$ in length.

In some embodiments, the lipid nanoparticle that encapsulates mRNA and includes DEPE as a helper lipid also includes a lipidoid that comprises alkyl chain(s) of $C_6$-$C_{20}$ length. In some embodiments, the lipidoid comprises alkyl chain(s) of $C_8$-$C_{16}$ length. In some embodiments, the lipidoid comprises alkyl chain(s) of $C_{10}$-$C_{14}$ length. In some embodiments, the lipidoid comprises alkyl chain(s) of $C_{10}$ length. In some embodiments, the lipidoid comprises alkyl chain(s) of $C_{12}$ length. In some embodiments, the lipidoid comprises alkyl chain(s) of $C_{16}$ length.

In certain embodiments, the lipid nanoparticle further comprising one or more sterols. In some embodiments, the one or more sterols is or comprises a cholesterol-based lipid, e.g., cholesterol or PEGylated cholesterol.

In some embodiment, the lipid nanoparticle comprises one or more cationic lipids, one or more PEG-modified lipids, one or more non-cationic lipids and one or more cholesterol-based lipids encapsulating the mRNA. For example, in a typical embodiment of the invention, the lipid components of the lipid nanoparticle comprise four types of lipids that include a cationic lipid (e.g., cKK-E12, Compound 1, Compound 2, or Compound 3), a PEG-modified lipid (e.g., DMG-PEG2K), a non-cationic lipid (DEPE) and a cholesterol-based lipid (e.g., cholesterol). In some embodiments, the ratio of cationic lipid(s) to non-cationic lipid(s) to cholesterol-based lipid(s) to PEG-modified lipid(s) in the lipid nanoparticle may be between about 30-60:25-35:20-30:1-15.

In some embodiment, the lipid components of the lipid nanoparticle comprise a cationic lipid (e.g., ICE), a PEG-modified lipid (e.g., DMG-PEG2K), a non-cationic lipid (DEPE). In some embodiments, the ratio of cationic lipid(s) to non-cationic lipid(s) to PEG-modified lipid(s) may be between about 50-60:45-30:5-10.

The mRNA being delivered by the lipid nanoparticles of the present invention is a mRNA encoding a protein that translates into the therapeutic protein in vivo. In certain embodiments, the mRNA encoding a protein encodes a polypeptide. In some embodiments, the polypeptide is a therapeutic polypeptide. In some embodiments, the therapeutic polypeptide is an antibody light chain or an antibody heavy chain. In some embodiments, the therapeutic polypeptide is a polypeptide absent or deficient in the subject. In certain embodiments, the mRNA encoding a protein encodes a peptide. In some embodiments, the peptide is an antigen.

In another aspect, the invention provides a method for improved delivery of mRNA to a subject in need thereof, the method comprising administering to the subject a lipid nanoparticle encapsulating the mRNA comprising one or more cationic lipids, one or more PEG-modified lipids and one or more helper lipids, wherein the one or more helper lipids comprises 1,2-Dierucoyl-sn-glycero-3-phosphoethanolamine (DEPE). The DEPE in the lipid nanoparticle provides for the enhanced expression of the mRNA when administered to the subject.

In some embodiments, an mRNA encodes a protein that translates into a therapeutic protein or peptide in vivo. In some embodiments, the mRNA encoding the protein or peptide is delivered systematically. In some embodiments, the translated protein or peptide is detectable in the liver at 6 hours or longer following administration. In some embodiments, the translated protein or peptide is detectable in the liver at 12 hours or longer following administration. In some embodiments, the translated protein or peptide is detectable in the liver at 18 hours or longer following administration. In some embodiments, the translated protein or peptide is detectable in the liver at 24 hours or longer following administration. In some embodiments, the translated protein or peptide is detectable in the liver at 36 hours or longer following administration. In some embodiments, the translated protein or peptide is detectable in the liver at 48 hours or longer following administration. In some embodiments, the translated protein or peptide is detectable in the liver at 72 hours or longer following administration. In some embodiments, the translated protein or peptide is detectable in the serum at 6 hours or longer following administration. In some embodiments, the translated protein or peptide is detectable in the serum at 12 hours or longer following administration. In some embodiments, the translated protein or peptide is detectable in the serum at 18 hours or longer following administration. In some embodiments, the translated protein or peptide is detectable in the serum at 24 hours or longer following administration. In some embodiments, the translated protein or peptide is detectable in the serum at 36 hours or longer following administration. In some embodiments, the translated protein or peptide is detectable in the serum at 48 hours or longer following administration. In some embodiments, the translated protein or peptide is detectable in the liver at 72 hours or longer following administration.

In a further aspect, the invention provides a lipid nanoparticle encapsulating a mRNA comprising one or more cationic lipids, one or more PEG-modified lipids and one or more helper lipids, wherein the one or more helper lipids comprises 1,2-Dierucoyl-sn-glycero-3-phosphoethanolamine (DEPE), for use in a method of treating or preventing a disease or disorder in a subject, wherein the mRNA encodes a peptide, polypeptide or protein that is suitable for treating or preventing the disease or disorder in the subject. In a related aspect, the invention relates to the use a lipid nanoparticle encapsulating an mRNA in the manufacture of a medicament for treating or preventing a disease or disorder in a subject, wherein the lipid nanoparticle comprise one or more cationic lipids, one or more PEG-modified lipids and one or more helper lipids, said one or more helper lipids comprising 1,2-Dierucoyl-sn-glycero-3-phosphoethanolamine (DEPE), and wherein the mRNA encodes a peptide, polypeptide or protein that is suitable for treating or preventing the disease or disorder in the subject. In one embodiment, the mRNA encodes a polypeptide or protein that is absent or deficient in the subject, wherein the disease or disorder is a deficiency in said polypeptide or protein. In another embodiment, the mRNA encodes an antibody light chain or an antibody heavy chain and the subject suffers from a disease or disorder that is treatable by administering an antibody comprising said light chain or said heavy chain to the subject. In a further embodiment, the mRNA encodes a peptide, polypeptide or protein, wherein said peptide, polypeptide or protein is capable of inducing an immune response in said subject in order to treat or prevent the disease or disorder.

The inventors also found that the use of DEPE as a helper lipid makes it possible to formulate multi-component formulations that do not form stable liposomes when DOPE is used as one of the helper lipids. In yet a further aspect, the invention therefore provides a method for preparing a lipid nanoparticle encapsulating a mRNA, said method comprising (a) providing a mixture of one or more cationic lipids, one or more PEG-modified lipids and one or more helper lipids, wherein the one or more helper lipids comprises 1,2-Dierucoyl-sn-glycero-3-phosphoethanolamine (DEPE), and (b) forming a lipid nanoparticle form the mixture provided in step (a), wherein the method further comprises encapsulating the mRNA into the lipid nanoparticle, wherein encapsulation can take place before or after formation of the lipid nanoparticle in step (b). The resulting lipid nanoparticle encapsulating the mRNA is stable. In one embodiment, the method for preparing a lipid nanoparticle in accordance with the invention specifically excludes the use of one or more helper lipids selected from dioleoylphosphatidylethanolamine (DOPE), 1,2-Dilinoleoyl-sn-glycero-3-phosphoethanolamine (DLOPE), 1-palmitoyl-2-oleoyl-sn-glycero-3-phosphoethanolamine (POPE), and combinations thereof. In one embodiment, the DEPE is present in the mixture at a concentration of between 10 molar percent and 50 molar percent. In one embodiment, the one or more PEG-modified lipids in the mixture comprises a poly(ethylene) glycol chain of up to 5 kDa in length covalently attached to a lipid with alkyl chain(s) of $C_6$-$C_{20}$ length. In one embodiment, the mixture one or more cationic lipids, one or more PEG-modified lipids and one or more helper lipids further comprises one or more sterols, such as a cholesterol-based lipid. In one embodiment, a cholesterol-based lipid is cholesterol and/or PEGylated cholesterol. In one embodiment, the mRNA encodes a therapeutic peptide, polypeptide or protein. In some embodiments, the mRNA is encapsulated into a preformed lipid nanoparticle. In some embodiments, the method for preparing a lipid nanoparticle in accordance with the invention further comprises subjecting the lipid nanoparticle to tangential flow filtration (TFF) before and/or after encapsulation of the mRNA. In some embodiments, the method further comprises formulating the lipid nanoparticle in a trehalose solution.

Without wishing to be bound by any particular theory, the inventors believe that DEPE derivatives, in particular, DEPE derivatives with varying lipid chain length or composition provide the same advantages as described herein for DEPE. For convenience, the foregoing summary and detailed description of the invention makes reference to DEPE only. It should be understood, however, that minor variations to the lipid chains of DEPE do not impact its superior properties and that such DEPE derivatives are expressly comprised within the invention.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

DETAILED DESCRIPTION OF THE INVENTION

Figure 1:
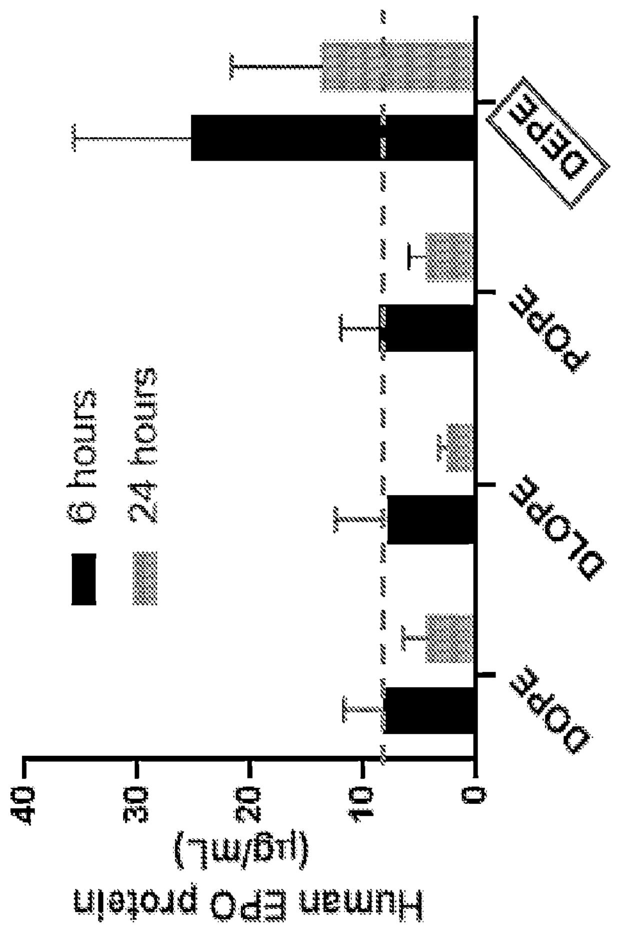
FIG. 1 depicts an exemplary graphical representation of the EPO protein expression in mRNA LNPs comprising DEPE and other helper lipids.

The following embodiments and aspects thereof are described and illustrated in conjunction with systems, compositions and methods which are meant to be exemplary and illustrative, not limiting in scope.

Definitions

The present invention provides an improved process for manufacturing mRNA encapsulated in lipid nanoparticle (LNP) formulations for producing mRNA therapeutic compositions.

In order for the present invention to be more readily understood, certain terms are first defined below. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Combining: As used herein, the term "combining" is interchangeably used with mixing or blending. Combining refers to putting together discrete LNP particles having distinct properties in the same solution, for example, combining an mRNA-LNP and an empty LNP, to obtain an mRNA-LNP composition. In some embodiments, the combining of the two LNPs is performed at a specific ratio of the components being combined. In some embodiments, the resultant composition obtained from the combining has a property distinct from any one or both of its components.

Delivery: As used herein, the term "delivery" encompasses both local and systemic delivery. For example, delivery of mRNA encompasses situations in which an mRNA is delivered to a target tissue and the encoded protein or peptide is expressed and retained within the target tissue (also referred to as "local distribution" or "local delivery"), and situations in which an mRNA is delivered to a target tissue and the encoded protein or peptide is expressed and secreted into patient's circulation system (e.g., serum) and systematically distributed and taken up by other tissues (also referred to as "systemic distribution" or "systemic delivery).

Efficacy: As used herein, the term "efficacy," or grammatical equivalents, refers to an improvement of a biologically relevant endpoint, as related to delivery of mRNA that encodes a relevant protein or peptide. In some embodiments, the biological endpoint is protecting against an ammonium chloride challenge at certain time points after administration.

Encapsulation: As used herein, the term "encapsulation," or grammatical equivalent, refers to the process of confining an individual mRNA molecule within a nanoparticle.

Expression: As used herein, "expression" of a mRNA refers to translation of an mRNA into a peptide (e.g., an antigen), polypeptide, or protein (e.g., an enzyme) and also can include, as indicated by context, the post-translational modification of the peptide, polypeptide or fully assembled protein (e.g., enzyme). In this application, the terms "expression" and "production," and grammatical equivalent, are used inter-changeably.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control sample" is a sample subjected to the same conditions as a test sample, except for the test article. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a peptide or protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one peptide, polypeptide or protein. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Potency: As used herein, the term "potency," or grammatical equivalents, refers to level of expression of protein(s) or peptide(s) that the mRNA encodes and/or the resulting biological effect.

Salt: As used herein the term "salt" refers to an ionic compound that does or may result from a neutralization reaction between an acid and a base.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutic Index: As used herein, "Therapeutic Index" is the ratio of the concentration of a drug in the blood at which it becomes toxic, and the concentration at which it is effective. The larger the therapeutic index, the safer the drug is.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Yield: As used herein, the term "yield" refers to the percentage of mRNA recovered after encapsulation as compared to the total mRNA as starting material. In some embodiments, the term "recovery" is used interchangeably with the term "yield".

Aliphatic: As used herein, the term aliphatic refers to $C_1$-$C_{40}$ hydrocarbons and includes both saturated and unsaturated hydrocarbons. An aliphatic may be linear, branched, or cyclic. For example, $C_1$-$C_{20}$ aliphatics can include $C_1$-$C_{20}$ alkyls (e.g., linear or branched $C_1$-$C_{20}$ saturated alkyls), $C_2$-$C_{20}$ alkenyls (e.g., linear or branched $C_4$-$C_{20}$ dienyls, linear or branched $C_6$-$C_{20}$ trienyls, and the like), and $C_2$-$C_{20}$ alkynyls (e.g., linear or branched $C_2$-$C_{20}$ alkynyls). $C_1$-$C_{20}$ aliphatics can include $C_3$-$C_{20}$ cyclic aliphatics (e.g., $C_3$-$C_{20}$ cycloalkyls, $C_4$-$C_{20}$ cycloalkenyls, or $C_8$-$C_{20}$ cycloalkynyls). In certain embodiments, the aliphatic may comprise one or more cyclic aliphatic and/or one or more heteroatoms such as oxygen, nitrogen, or sulfur and may optionally be substituted with one or more substituents such as alkyl, halo, alkoxyl, hydroxy, amino, aryl, ether, ester or amide. An aliphatic group is unsubstituted or substituted with one or more substituent groups as described herein. For example, an aliphatic may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R' independently is unsubstituted $C_1$-$C_3$ alkyl. In embodiments, the aliphatic is unsubstituted. In embodiments, the aliphatic does not include any heteroatoms.

Alkyl: As used herein, the term "alkyl" means acyclic linear and branched hydrocarbon groups, e.g. "$C_1$-$C_{20}$ alkyl" refers to alkyl groups having 1-20 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentylhexyl, Isohexyl etc. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R' independently is unsubstituted $C_1$-$C_3$ alkyl. In embodiments, the alkyl is substituted (e.g., with 1, 2, 3, 4, 5, or 6 substituent groups as described herein). In embodiments, an alkyl group is substituted with a-OH group and may also be referred to herein as a "hydroxyalkyl" group, where the prefix denotes the —OH group and "alkyl" is as described herein.

Alkenyl: As used herein, "alkenyl" means any linear or branched hydrocarbon chains having one or more unsaturated carbon-carbon double bonds that may occur in any stable point along the chain, e.g. "$C_2$-$C_{20}$ alkenyl" refers to an alkenyl group having 2-20 carbons. For example, an alkenyl group includes prop-2-enyl, but-2-enyl, but-3-enyl, 2-methylprop-2-enyl, hex-2-enyl, hex-5-enyl, 2,3-dimethylbut-2-enyl, and the like. In embodiments, the alkenyl comprises 1, 2, or 3 carbon-carbon double bond. In embodiments, the alkenyl comprises a single carbon-carbon double bond. In embodiments, multiple double bonds (e.g., 2 or 3) are conjugated. An alkenyl group may be unsubstituted or substituted with one or more substituent groups as described herein. For example, an alkenyl group may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —$N(R')_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R' independently is an unsubstituted alkyl (e.g., unsubstituted $C_1$-$C_{20}$ alkyl, $C_1$-$C_{15}$ alkyl, $C_1$-$C_{10}$ alkyl, or $C_1$-$C_3$ alkyl). In embodiments, R' independently is unsubstituted $C_1$-$C_3$ alkyl. In embodiments, the alkenyl is unsubstituted. In embodiments, the alkenyl is substituted (e.g., with 1, 2, 3, 4, 5, or 6 substituent groups as described herein). In embodiments, an alkenyl group is substituted with a-OH group and may also be referred to herein as a "hydroxyalkenyl" group, where the prefix denotes the —OH group and "alkenyl" is as described herein.

Alkynyl: As used herein, "alkynyl" means any hydrocarbon chain of either linear or branched configuration, having one or more carbon-carbon triple bonds occurring in any stable point along the chain, e.g. "$C_2$-$C_{20}$ alkynyl" refers to an alkynyl group having 2-20 carbons. Examples of an alkynyl group include prop-2-ynyl, but-2-ynyl, but-3-ynyl, pent-2-ynyl, 3-methylpent-4-ynyl, hex-2-ynyl, hex-5-ynyl, etc. In embodiments, an alkynyl comprises one carbon-carbon triple bond. An alkynyl group may be unsubstituted or substituted with one or more substituent groups as described herein. For example, an alkynyl group may be substituted with one or more (e.g., 1, 2, 3, 4, 5, or 6 independently selected substituents) of halogen, —COR', —$CO_2$H, —$CO_2$R', —CN, —OH, —OR', —OCOR', —$OCO_2$R', —$NH_2$, —NHR', —N(R')$_2$, —SR' or —$SO_2$R', wherein each instance of R' independently is $C_1$-$C_{20}$ aliphatic (e.g., $C_1$-$C_{20}$ alkyl, $C_1$-$C_{15}$ alkyl, $C_1$-$C_{10}$ alkyl, or $C_1$-$C_3$ alkyl). In embodiments, R' independently is an unsubstituted alkyl (e.g., unsubstituted $C_1$-$C_{20}$alkyl, $C_1$-$C_{15}$ alkyl, $C_1$-$C_{10}$ alkyl, or $C_1$-$C_3$ alkyl). In embodiments, R' independently is unsubstituted $C_1$-$C_3$ alkyl. In embodiments, the alkynyl is unsubstituted. In embodiments, the alkynyl is substituted (e.g., with 1, 2, 3, 4, 5, or 6 substituent groups as described herein).

Aryl: The term "aryl" used alone or as part of a larger moiety as in "aralkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. In embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Exemplary aryls include phenyl, naphthyl, and anthracene.

Arylene: The term "arylene" as used herein refers to an aryl group that is divalent (that is, having two points of attachment to the molecule). Exemplary arylenes include phenylene (e.g., unsubstituted phenylene or substituted phenylene).

Compositions of the Invention

In some embodiments, the invention provides compositions comprising LNP and mRNA, which when administered to a subject, induce significantly higher levels of mRNA expression in vivo, without altering the subject's tolerance or stress level. The tolerance or stress is determined by elevation of liver enzymes aspartate transaminase (AST) and/or alanine aminotransferase (ALT). In some embodiments, the specific formulations provide manufacturing advantages, such as ease of manufacturing process, e.g., utilization of common preformed LNP stock solutions, among others.

The observations of the present invention revealed that when mRNA-LNPs formed by mixing mRNA with preformed empty LNPs in a step (a) were further combined with preformed LNPs in a step (b) to form a mRNA-LNP composition, the potency of the resultant composition is greatly increased compared to the mRNA-LNP of step (a). This is particularly worth-noting since the increased potency is observed even when the preformed LNPs are empty (i.e., do not comprise an mRNA) and comprise the same lipid components as the mRNA-LNP. Moreover, even in the case where the preformed LNP comprise only neutral lipids, which are known to be poor facilitators of polynucleotide transfection, an increased expression of the mRNA encoded protein is observed.

Therefore, the fact that increased potency of the mRNA-LNP composition is achievable without compromising the in vivo tolerability is a striking advantage of the method of the invention in terms of therapeutic design.

This aspect of the invention allows for at least two significant advantages, (i) providing for lower amount of mRNA in an mRNA therapeutic composition per dose, or lowering the dosing frequency in order to achieve the same biological effect, thereby increasing the therapeutic index of the composition; (ii) developing an easy, flexible, scalable and/or high throughput manufacturing process where one or more preformed LNPs can be prepared in bulk and made available for multiple mixing and combining steps for achieving the desired formulations as described in the invention.

The present invention provides for a process, where mRNA-LNPs prepared by mixing mRNA with preformed empty LNPs are further combined with preformed LNPs, wherein the resultant mRNA-LNP composition of the invention results in increased in vivo expression of the mRNA encoded protein. In some aspects, this process is a manufacturing process comprising the steps of (a) mixing preformed empty LNPs with mRNA under conditions that allow formation of mRNA-LNPs; (b) combining the mRNA-LNPs formed in step (a) with preformed LNPs, thereby manufacturing a composition comprising lipid nanoparticles encapsulating mRNA. In some embodiments, the lipid nanoparticles comprise at least a cationic lipid, a non-cationic lipid and a PEG-modified lipid. In some embodiments, a lipid nanoparticle may comprise a neutral lipid, with or without a cationic lipid.

In some embodiments, the mRNA encodes for a protein or a peptide.

In some embodiments, the preformed LNP in step (b) is an empty LNP. In some embodiments, the preformed LNP in step (b) comprise mRNA. In some embodiments, the preformed LNP in step (b) comprise mRNA that encodes for a protein or a peptide. In some embodiments, the preformed LNP in step (b) comprises the same mRNA encoding the same protein or polypeptide as in the mRNA-LNP formed in step (a). In some embodiments, the preformed LNP in step (b) comprises a different mRNA that encodes a different protein or polypeptide than in the mRNA-LNPs formed in step (a).

In some embodiments, the empty LNP in step (a) and the preformed LNP in step (b) are distinct, heterogeneous lipid nanoparticles. For example, the empty LNP in step (a) may comprise a cationic lipid HGT-5003, and the preformed LNP in step (b) comprise a cationic lipid ICE. In another example, the empty LNP in step (a) may comprise a cationic lipid ICE, and the preformed LNP in step (b) comprise a cationic lipid DOTAP. In yet another example, the empty LNP in step (a) may comprise a cationic lipid HGT-4001, and the preformed LNP in step (b) comprise a cationic lipid ckk-E12. The various lipids suitable for LNPs and methods for generating the same are described in the respective section below, and any combination of the lipids to form the LNPs are contemplated herein.

In one embodiment, the mRNA-LNP composition generated in step (b) may comprise a first lipid nanoparticle and a second lipid nanoparticle; wherein the first lipid nanoparticle and the second lipid nanoparticle have identical lipid compositions, where at least some first lipid nanoparticles comprise an mRNA. In one embodiment, the mRNA-LNP composition generated in step (b) may comprise a first lipid nanoparticle and a second lipid nanoparticle; wherein the first lipid nanoparticle and the second lipid nanoparticle have distinct lipid compositions. For example, the mRNA-LNP composition may comprise a first lipid nanoparticle comprising the cationic lipid ICE and a second lipid nanoparticle that comprises the cationic lipid DOTAP. In some embodiments, the mRNA-LNP composition generated in step (b) may comprise a first lipid nanoparticle that comprises the cationic lipid $C_{12}$-$C_{20}$ and a second lipid nanoparticle that comprises the cationic lipid DLinKC2DMA. Accordingly, any combination of the various lipids suitable for generating LNPs as described in the respective sections below are contemplated herein.

In some embodiments, either the empty LNP of step (a) or the preformed LNP of step (b) does not comprise a cationic lipid. In some embodiments, either the empty LNP or the preformed LNP comprises a neutral lipid and/or a PEG-modified lipid.

Lipid Nanoparticles (LNP)

The present invention provides, among others, a composition for an mRNA therapeutic where the mRNA is encapsulated in a delivery vehicle for efficient cellular uptake and processing in vivo. As used herein, the terms "delivery vehicle," "transfer vehicle," "nanoparticle" or grammatical equivalent, are used interchangeably. Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

In some embodiments, a suitable delivery vehicle is a liposomal delivery vehicle, e.g., a lipid nanoparticle (LNP) or liposome. In some embodiments, liposomes comprise one or more cationic lipids. In some embodiments, a liposome comprises one or more cationic lipids, one or more non-cationic lipids, one or more cholesterol-based lipids and one or more PEG-modified lipids. In some embodiments, a liposome comprises one or more cationic lipids, one or more non-cationic lipids, and one or more PEG-modified lipids. In some embodiments, a liposome comprises no more than four distinct lipid components. In some embodiments, a liposome comprises no more than three distinct lipid components. In some embodiments, one distinct lipid component is a sterol-based cationic lipid. In a typical embodiment, the LNP of the invention is a liposome encapsulating a mRNA. The lipid components of a suitable liposome comprise a cationic lipid (e.g., cKK-E12, Compound 1, Compound 2 or Compound 3), a non-cationic lipid (DEPE), a cholesterol-based lipid (e.g., cholesterol) and a PEG-modified lipid (DMG-PEG2K). Alternatively, the lipid components of a suitable liposome comprise a sterol-based cationic lipid (e.g., ICE), a non-cationic lipid (DEPE) and a PEG-modified lipid (e.g., DMG-PEG2K).

In some embodiments, the DEPE in the lipid nanoparticle provides for enhanced expression of the mRNA encoding a protein or a peptide, in particular in comparison to a DOPE-containing lipid nanoparticle that is otherwise identical in composition (in terms of lipid components and molar ratio of the individual lipid components) to the DEPE-containing lipid nanoparticle. In some embodiments, expression of the mRNA encoding protein delivered by a DEPE-containing lipid nanoparticle is enhanced at least two-fold relative to a DOPE-containing lipid nanoparticle. Enhanced expression of the mRNA can be determined by administering a DEPE-containing lipid nanoparticle and an identically formulated lipid nanoparticle with a different helper lipid (e.g., DOPE) to test animals (e.g., a mouse), for instance by tail vein injection, and monitoring expression of the mRNA at one or more time points (e.g., at 4, 6, 8, 12, 18 or 24 hours post administration).

In some embodiments, mRNA encodes for a protein that translates into the therapeutic protein in vivo. In some embodiments, the mRNA encoding a protein encodes a polypeptide. In some embodiments, the polypeptide is a therapeutic polypeptide. In some embodiments, the therapeutic polypeptide is an antibody light chain or an antibody heavy chain. In some embodiments, the therapeutic polypeptide is absent or deficient in the subject to which the mRNA is administered. In some embodiments, the mRNA encoding a protein encodes a peptide. In some embodiments, the peptide is an antigen.

In some embodiments, the DEPE-containing lipid nanoparticles of the invention are safe and tolerable when administered to a subject. For example, the DEPE-containing lipid nanoparticles of the invention do not result in any discemable liver toxicity when administered to subject. Suitable markers for assessing liver toxicity are ALT and AST.

Cationic Lipids

As used herein, the phrase "cationic lipids" refers to any of a number of lipid species that have a net positive charge at a selected pH, such as physiological pH.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of

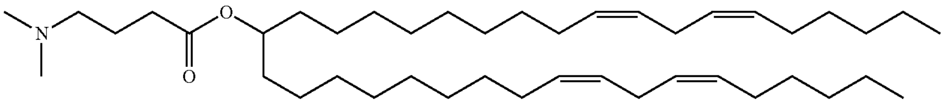 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

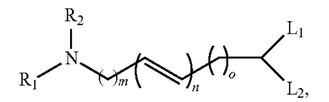

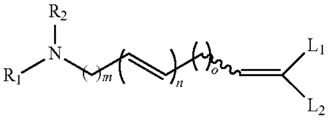

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of (HGT-5002)

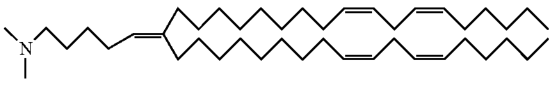

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

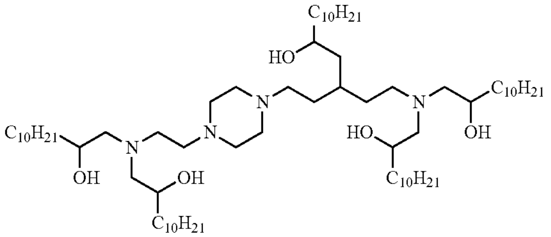

and pharmaceutically acceptable salts thereof.

In some embodiments, lipidoids used in the compositions and methods of the invention include are synthesized by (HGT-5000)

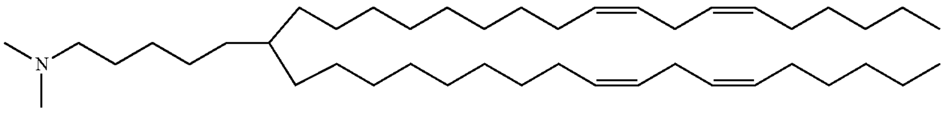

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of (HGT-5001)

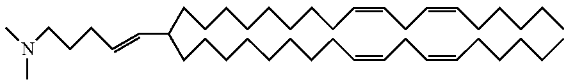

reacting commercially available amines with lipophilicacrylates, acrylamides, or epoxides. In some embodiments, lipidoids are derived from amine 86 (N,N-Bis(2-hydroxyethyl) ethylene diamine) and amine 87 (N-(3-aminopropyl) diethaneamine). The lipidoids have several advantages as a potential new class of nucleic acid delivery reagents: (i) the chemistry used to synthesize lipidoids is simple and economical, (ii) a library of structural diversity was already developed, (iii) a correlation between structure and function of delivery systems could be constructed from the large data sets accumulated from screening the library of lipidoids. The simplicity of these reactions allowed to build a structurally diverse library of lipidoids by varying the types of amines, and the lengths and types (acrylamide/acrylate/epoxide) of tails (or carbon-arm chains).

In some embodiments, lipidoids comprise about 2-20 carbon-arm chains. In some embodiments, lipidoids comprise about 5-18 carbon-arm chains. In some embodiments, lipidoids comprise about 10-16 carbon-arm chains. In some embodiments lipidoids comprise about 10-14 carbon-arm chains. In some embodiments, lipidoids comprise about 10-12 carbon-arm chains. In some embodiments, lipidoids comprise about 10 carbon-arm chains. In some embodiments, lipidoids comprise about 12 carbon-arm chains. In some embodiments, lipidoids comprise about 14 carbon-arm chains. In some embodiments, lipidoids comprise about 16 carbon-arm chains.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

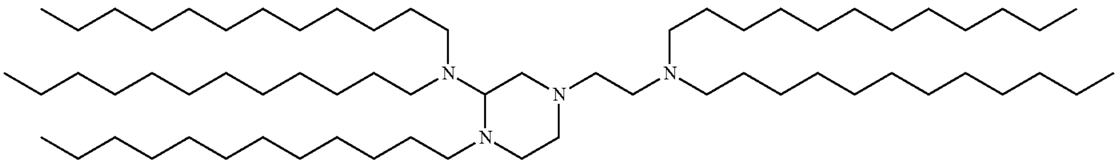 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of

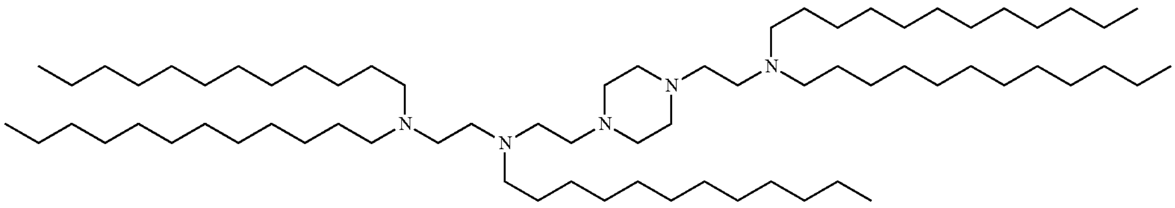 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

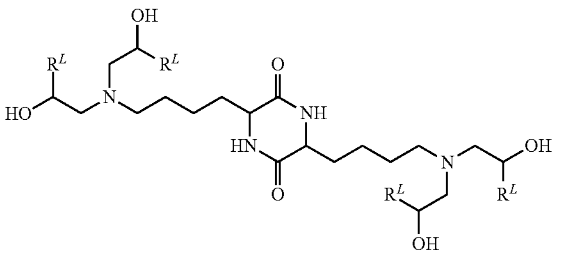

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

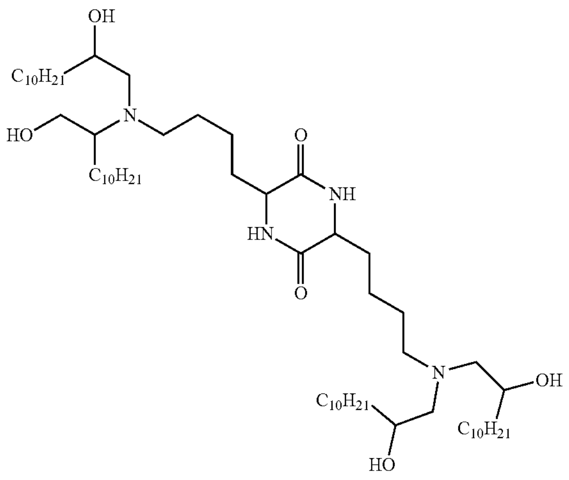

and pharmaceutically acceptable salts thereof. In certain embodiments, the compositions and methods of the present invention include a cationic lipid having a compound structure of:

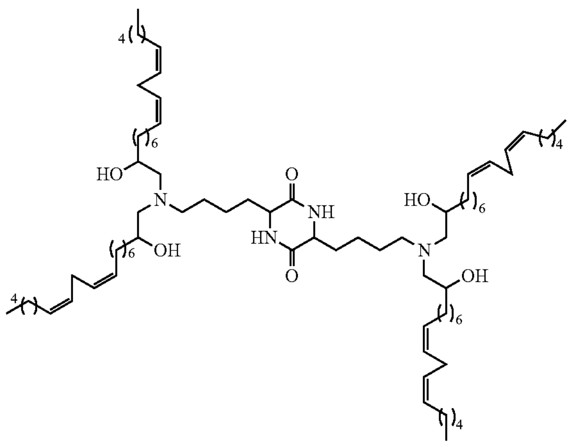

and pharmaceutically acceptable salts thereof. In certain embodiments, the compositions and methods of the present invention include a cationic lipid having a compound structure of:

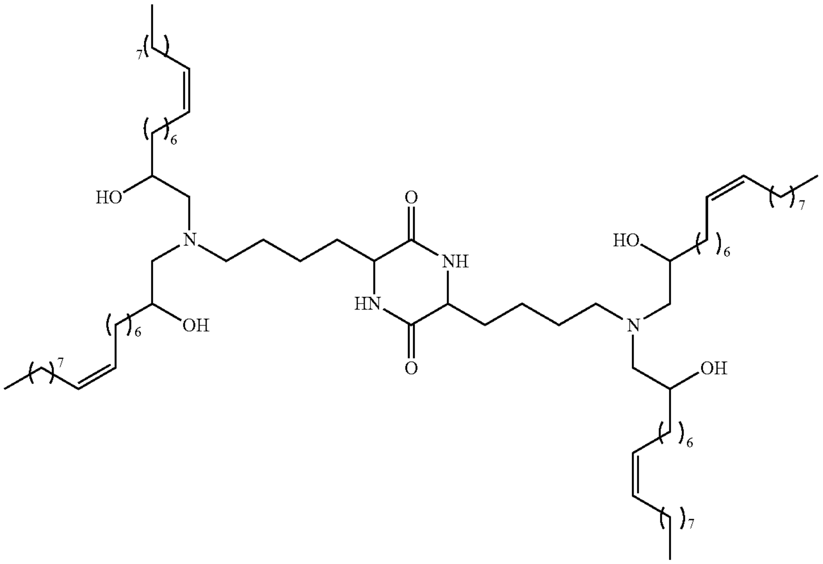

and pharmaceutically acceptable salts thereof. In certain embodiments, the compositions and methods of the present invention include a cationic lipid having a compound structure of:

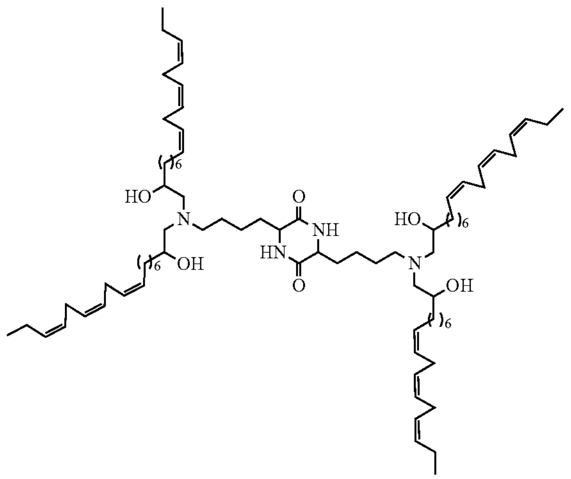

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

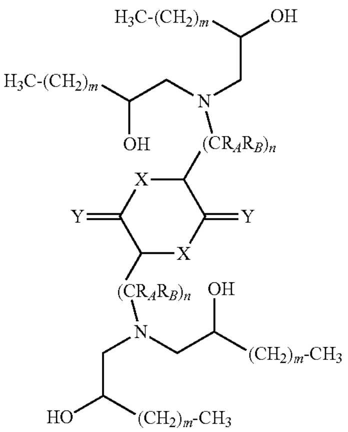

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

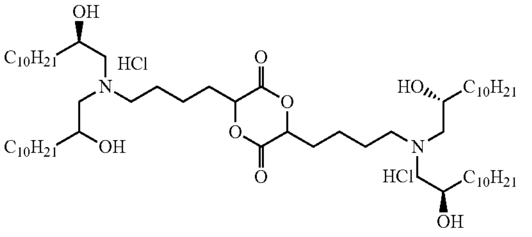

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

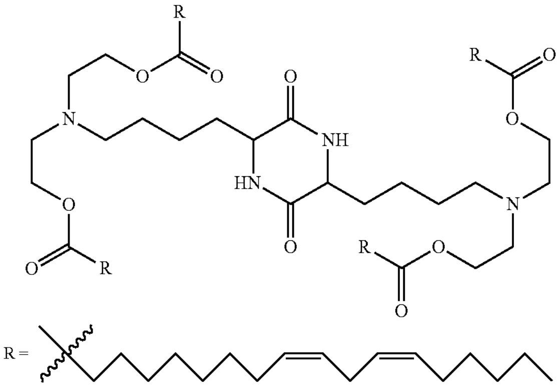

or a pharmaceutically acceptable salt thereof. In some embodiments, the compositions and methods of the present invention include a cationic lipid having the compound structure:

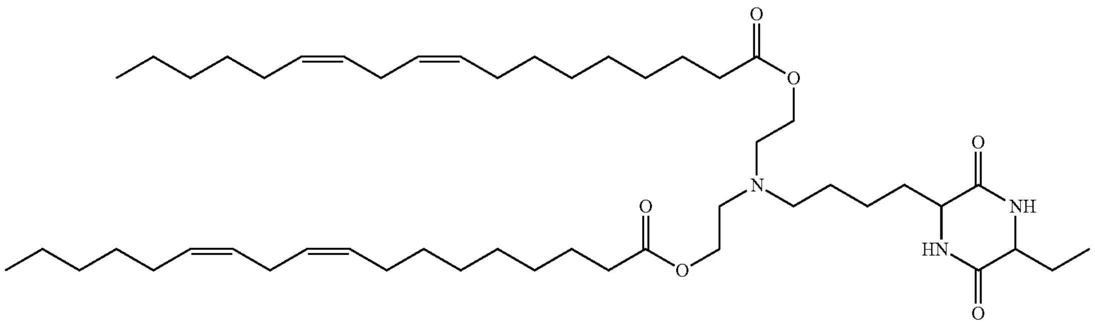 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

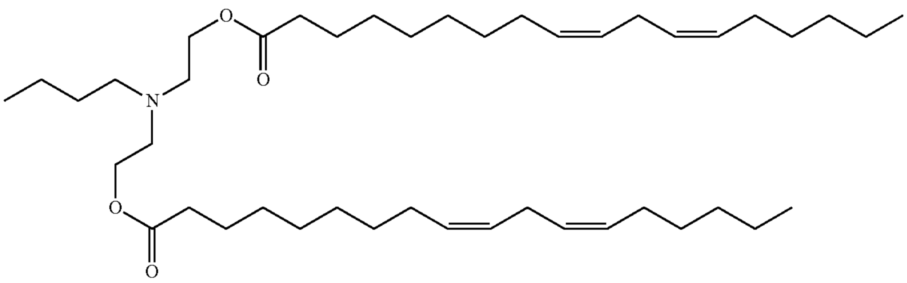 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include cationic lipids as described in U.S. Provisional Patent Application Ser. No. 62/758,179, which is incorporated herein by reference. In some embodiments, the compositions and methods of the present invention include a cationic lipid of the following formula:

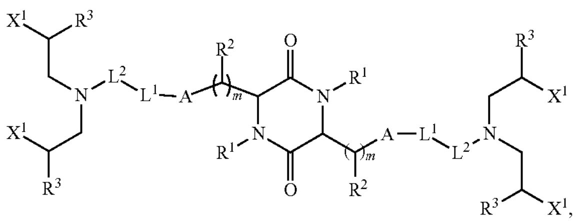

or a pharmaceutically acceptable salt thereof, wherein each $R^1$ and $R^2$ is independently H or $C_1$-$C_6$ aliphatic; each m is independently an integer having a value of 1 to 4; each A is independently a covalent bond or arylene; each $L^1$ is independently an ester, thioester, disulfide, or anhydride group; each $L^2$ is independently $C_2$-$C_{10}$ aliphatic; each $X^1$ is independently H or OH; and each $R^3$ is independently $C_6$-$C_{20}$ aliphatic. In some embodiments, the compositions and methods of the present invention include a cationic lipid of the following formula:

(Compound 1)

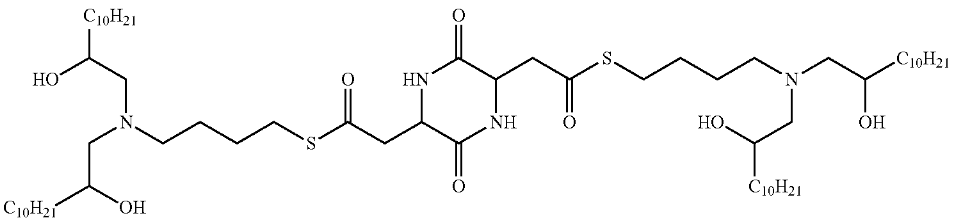

or a pharmaceutically acceptable salt thereof. In some embodiments, the compositions and methods of the present invention include a cationic lipid of the following formula:

(Compound 2)

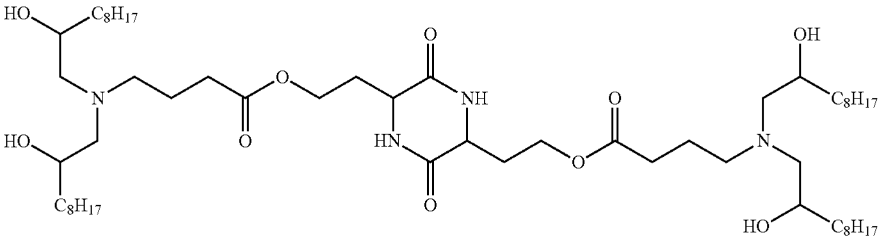

or a pharmaceutically acceptable salt thereof. In some embodiments, the compositions and methods of the present invention include a cationic lipid of the following formula:

(Compound 3)

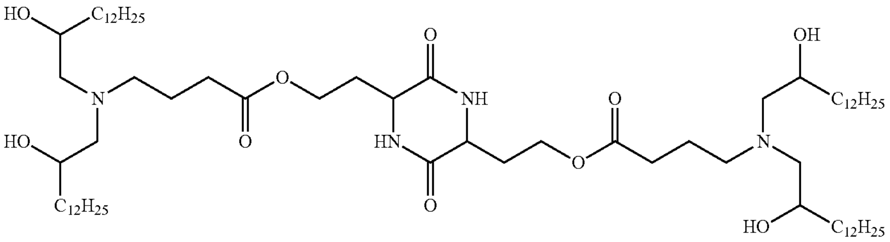

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

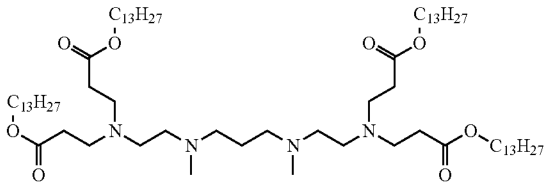

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

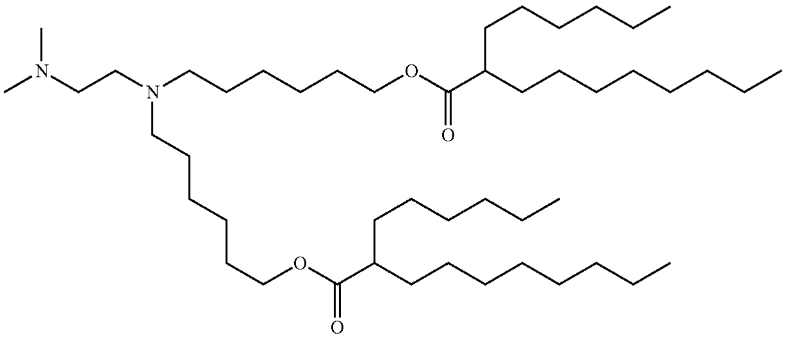 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

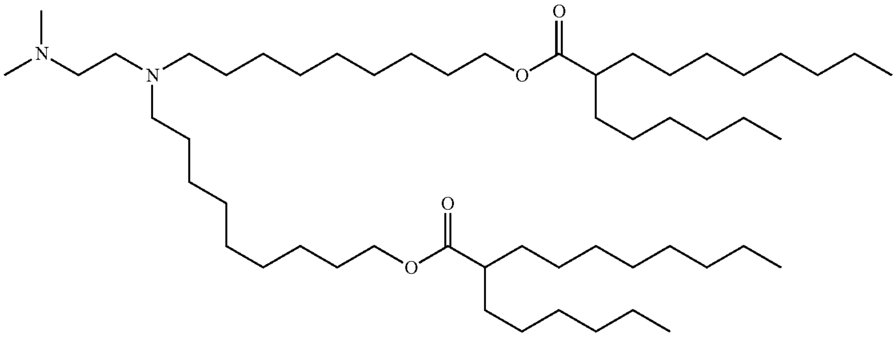 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

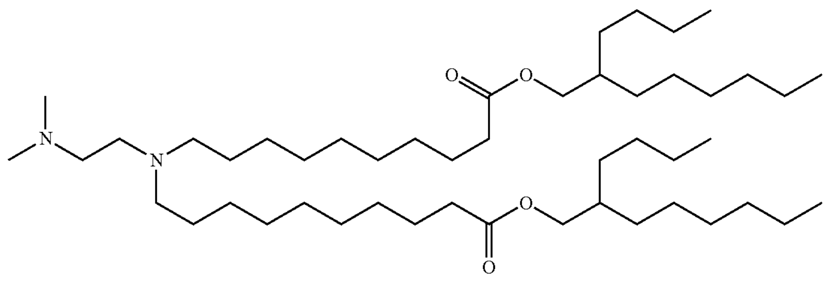 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

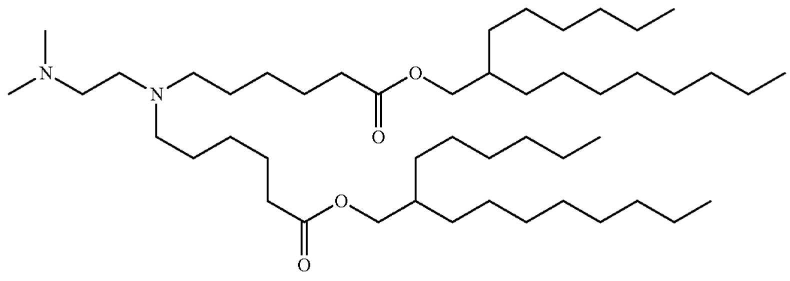 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

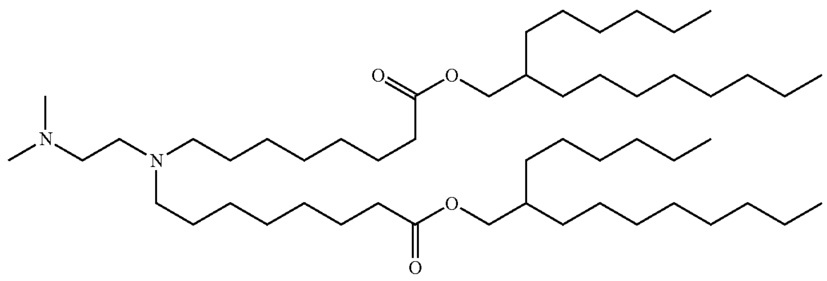 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

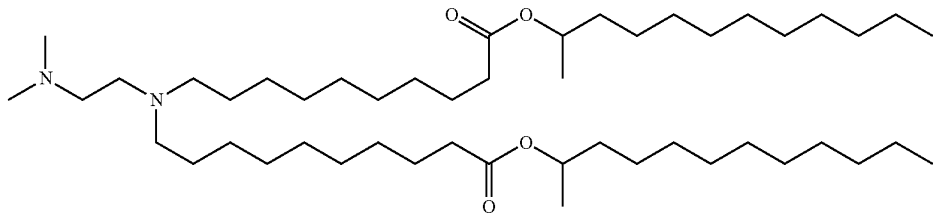 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

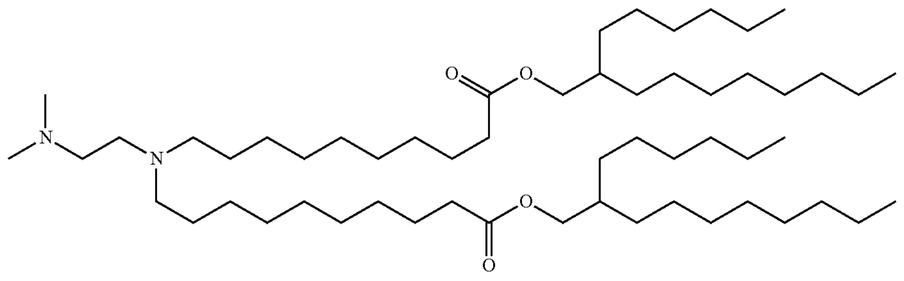 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

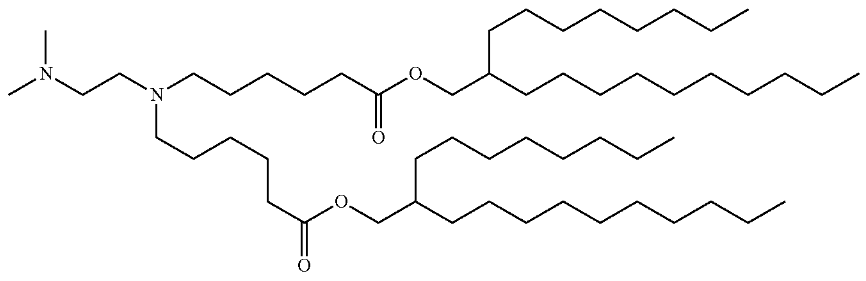 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

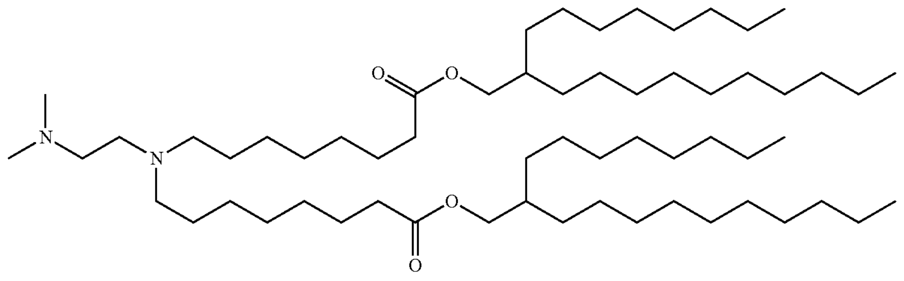 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

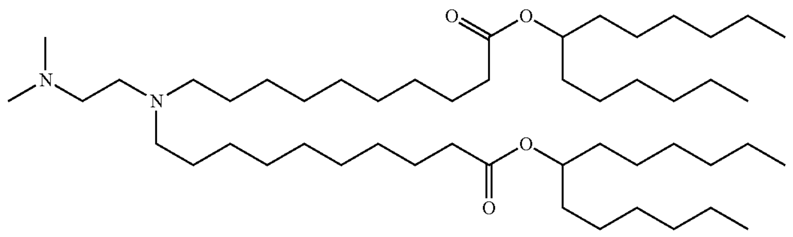 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

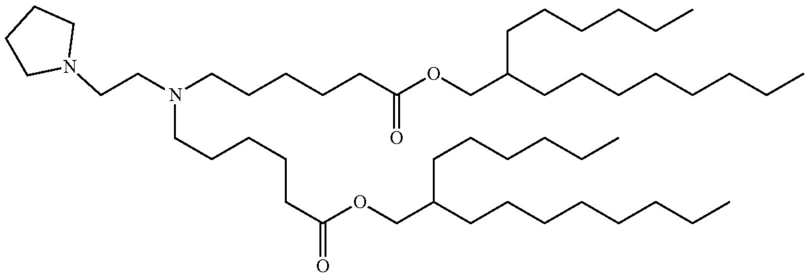 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

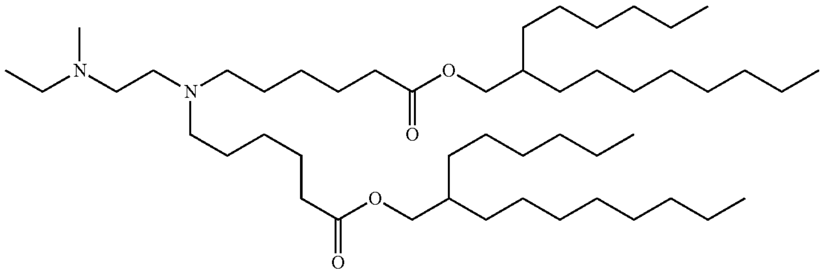 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

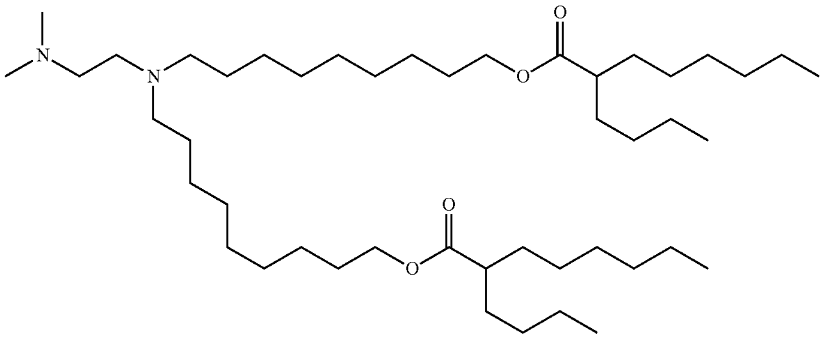 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

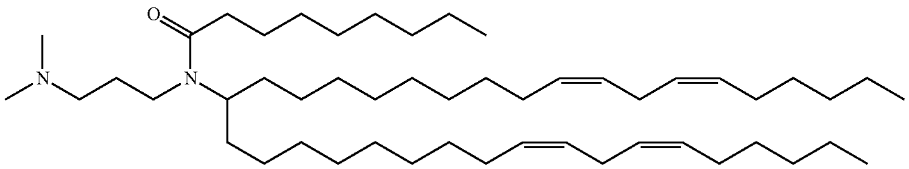 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

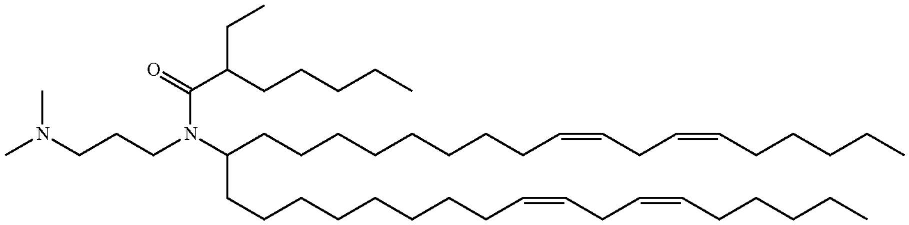 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

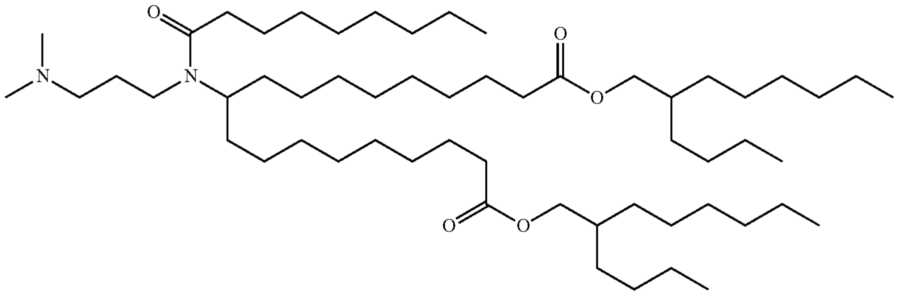 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

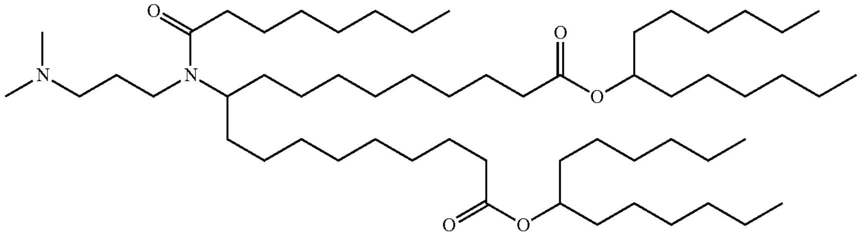 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

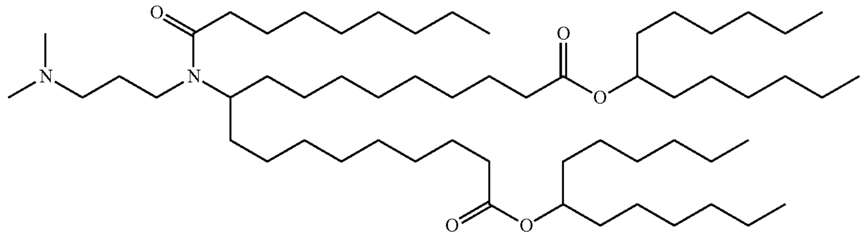 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

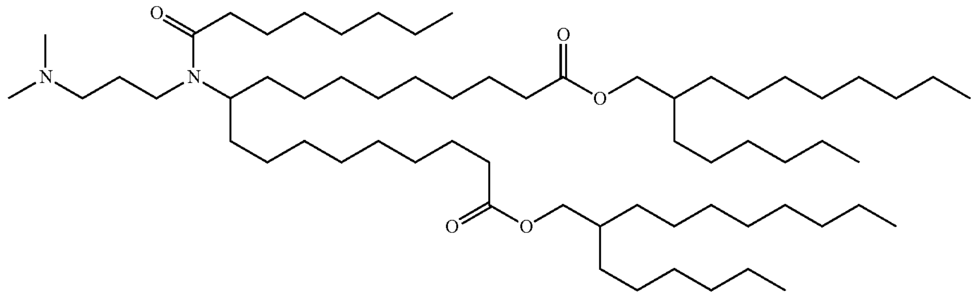 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

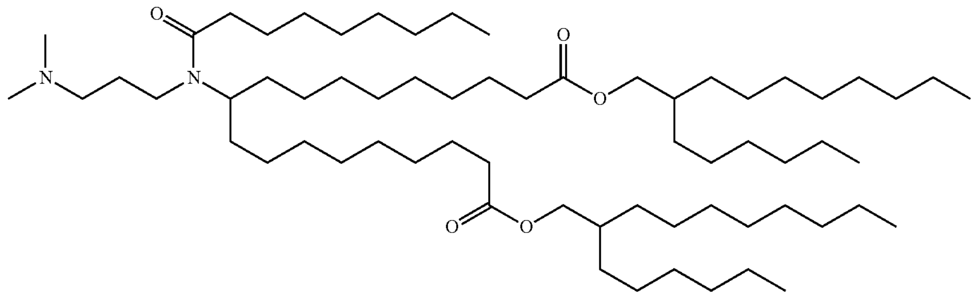 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

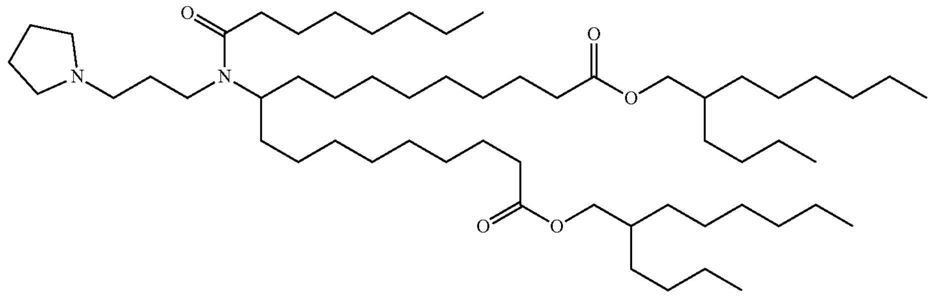 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

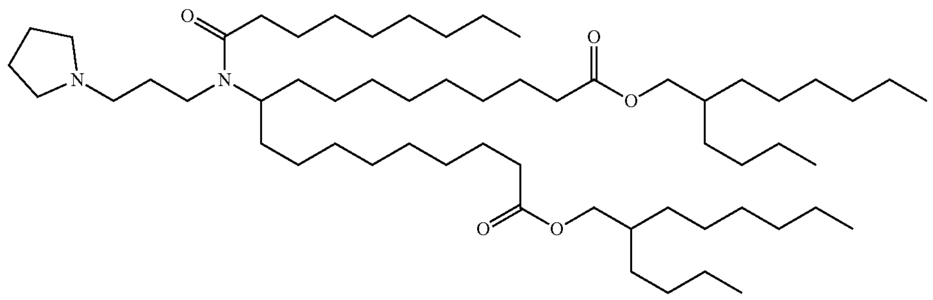 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

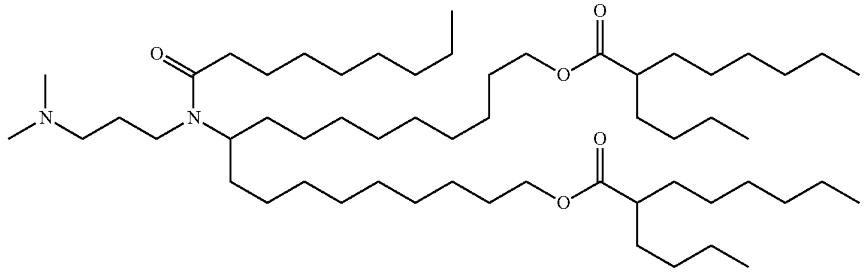 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

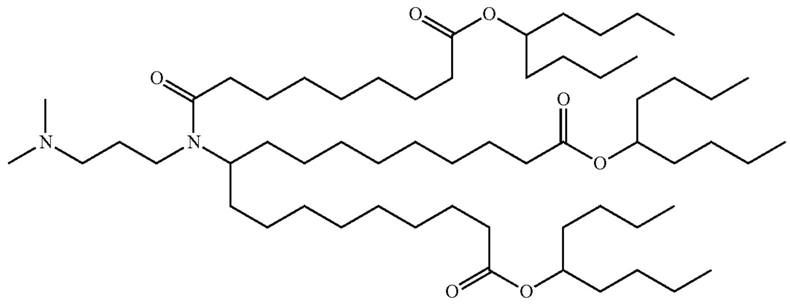 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

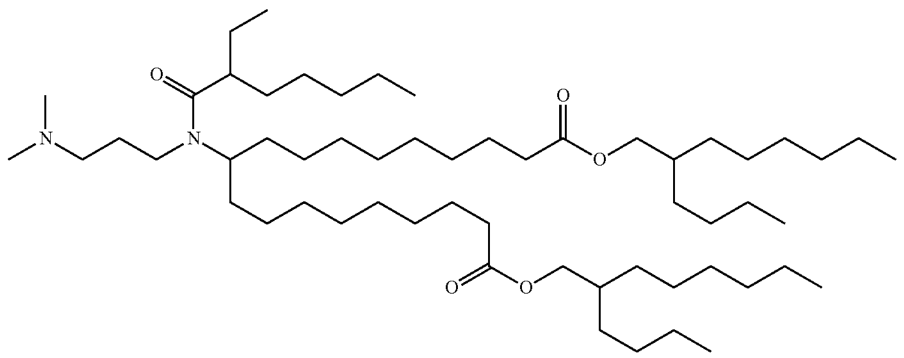 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

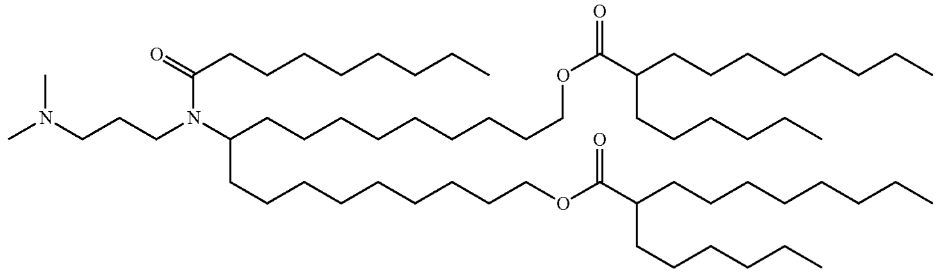 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

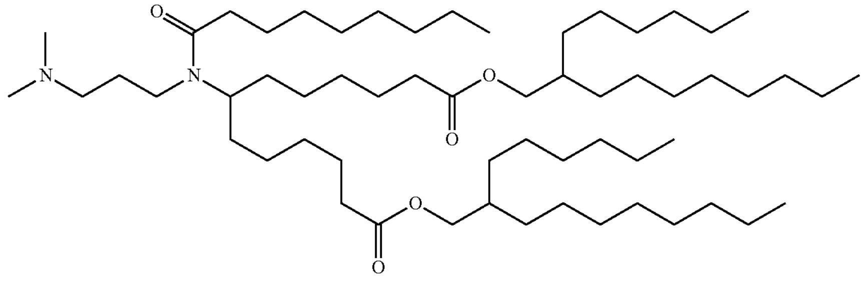 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

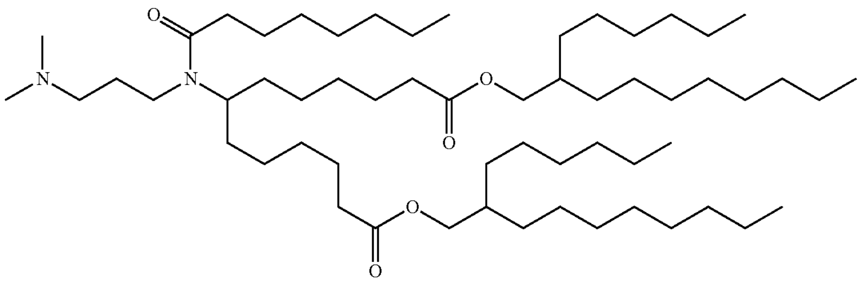 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

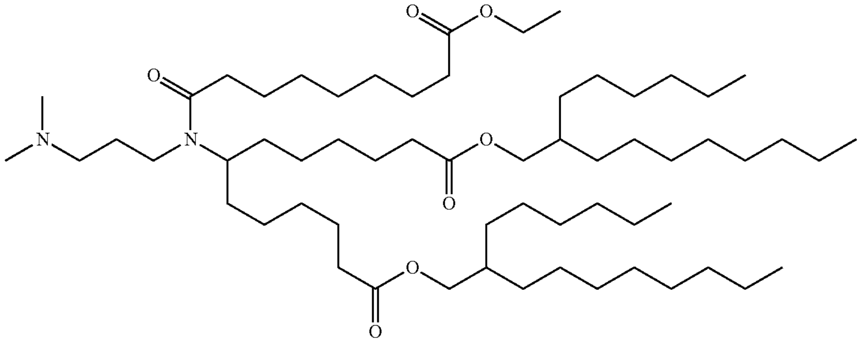 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

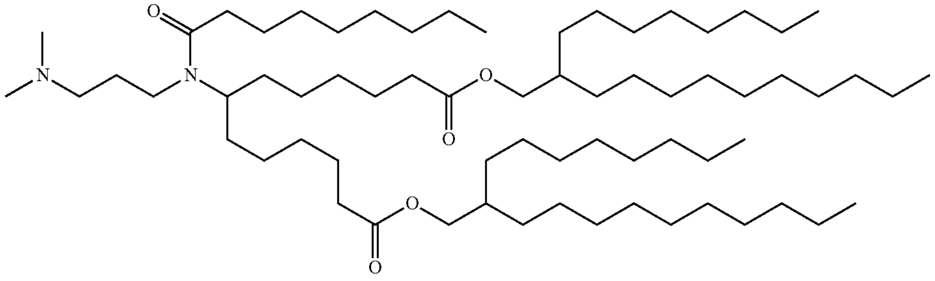 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

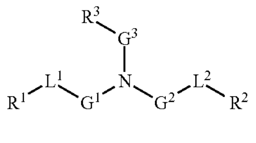

or a pharmaceutically acceptable salt thereof, wherein one of $L^1$ or $L^2$ is —O(C═O)—, —(C═O)O—, —C(═O)—, —O—, —$S(O)_x$—, —S—S—, —C(═O)S—, —SC(═O)—, —$NR^a$C(═O)—, —C(═O)$NR^a$—, $NR^a$C(═O)$NR^a$—, —OC(═O)$NR^a$—, or —$NR^a$C(═O)O—; and the other of $L^1$ or $L^2$ is —O(C═O)—, —(C═O)O—, —C(═O)—, —O—, —$S(O)_x$, —S—S—, —C(═O)S—, SC(═O)—, —$NR^a$C(═O)—, —C(═O)$NR^a$—, $NR^a$C(═O)$NR^a$—, —OC(═O)$NR^a$— or —$NR^a$C(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)$OR^4$, —OC(═O)$R^4$ or —$NR^5$ C(═O)$R^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

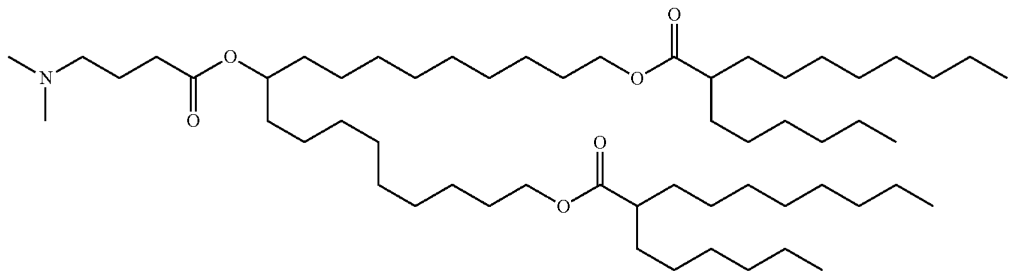 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

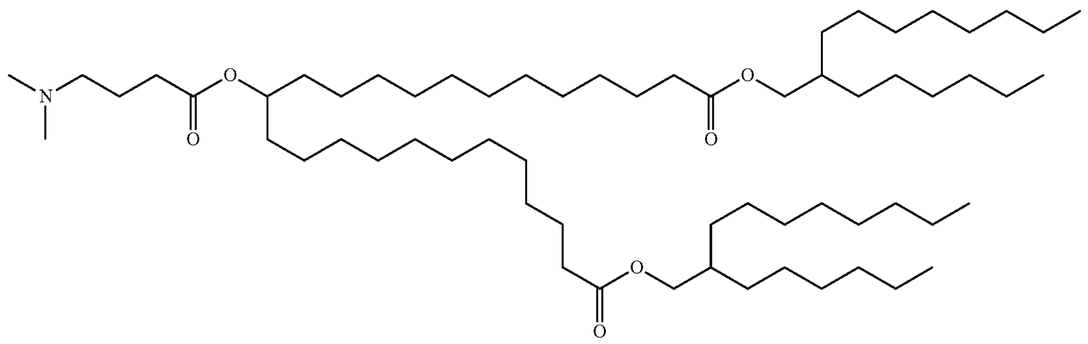 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

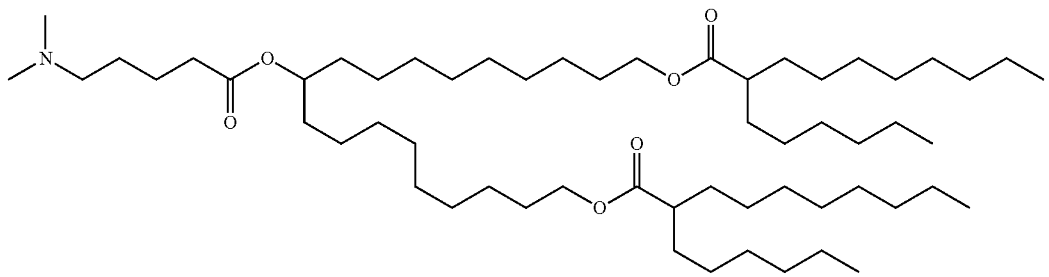 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

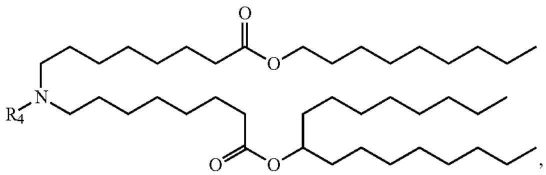

,

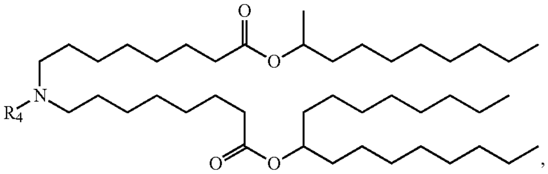

,

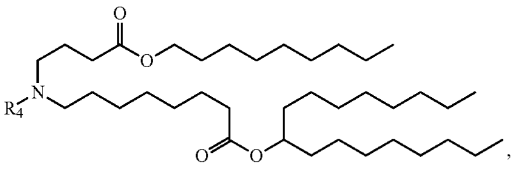

, and

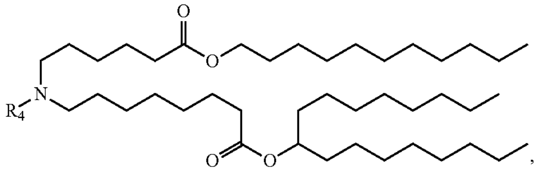

, and pharmaceutically acceptable salts thereof. For any one of these four formulas, $R_4$ is independently selected from $-(CH_2)_nQ$ and $-(CH_2)_nCHQR$; Q is selected from the group consisting of $-OR$, $-OH$, $-O(CH_2)_nN(R)_2$, $-OC(O)R$, $-CX_3$, $-CN$, $-N(R)C(O)R$, $-N(H)C(O)R$, $-N(R)S(O)_2R$, $-N(H)S(O)_2R$, $-N(R)C(O)N(R)_2$, $-N(H)C(O)N(R)_2$, $-N(H)C(O)N(H)(R)$, $-N(R)C(S)N(R)_2$, $-N(H)C(S)N(R)_2$, $-N(H)C(S)N(H)(R)$, and a heterocycle; and n is 1, 2, or 3. In certain embodiments, the compositions and methods of the present invention include a cationic lipid having a compound structure of:

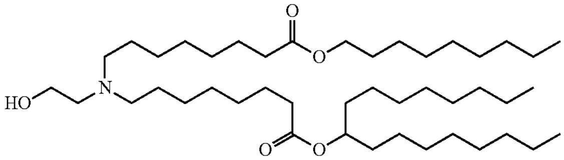 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

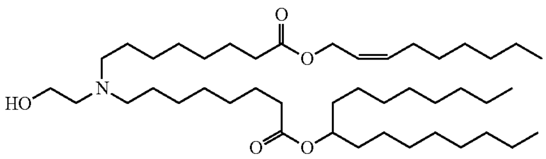 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

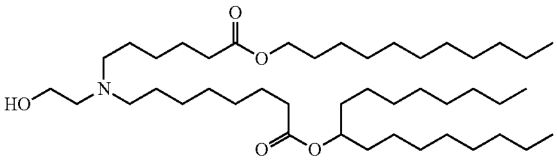 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

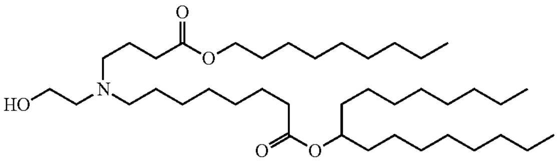 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of

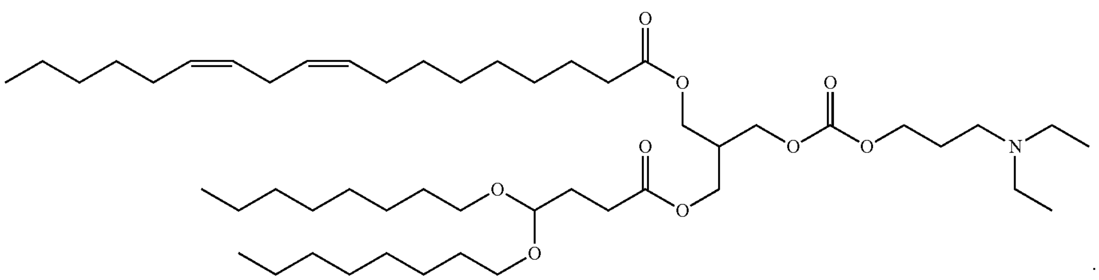 [SMILES: CCCCC/C=C\C/C=C\CCCCCCCC(=O)OCC(COC(=O)CCC(OCCCCCCCC)OCCCCCCCC)COC(=O)OCCCN(CC)CC]

.

and pharmaceutically acceptable salts thereof. In certain embodiments, the compositions and methods of the present invention include a cationic lipid having a compound structure of

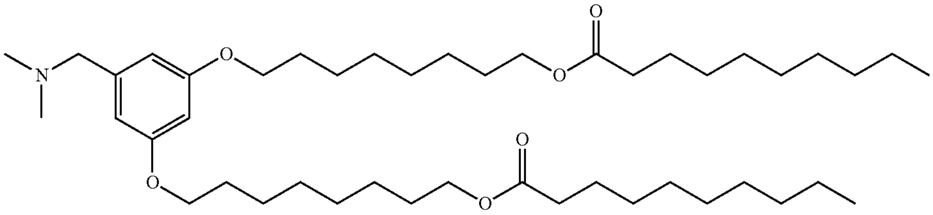 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of

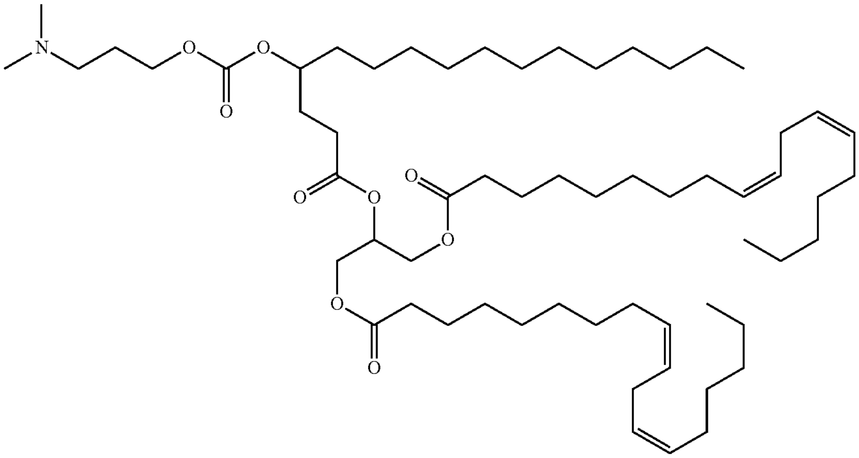 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of

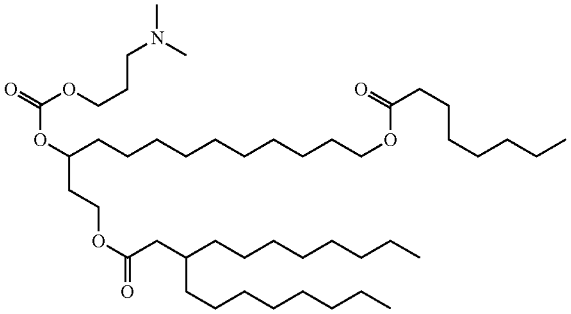 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

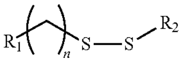, wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

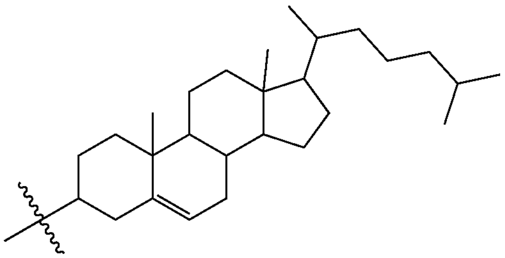

and

-continued

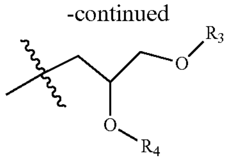

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, “HGT4001”, having a compound structure of (HGT4001)

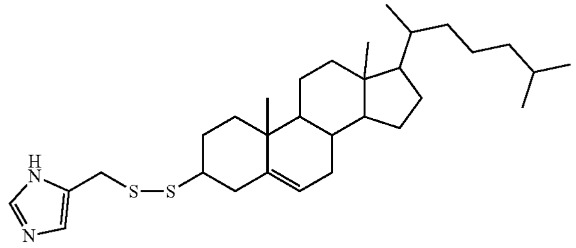

and pharmaceutically acceptable salts thereof. In certain embodiments, the compositions and methods of the present invention include a cationic lipid, “HGT4002”, having a compound structure of:

(HGT4002)

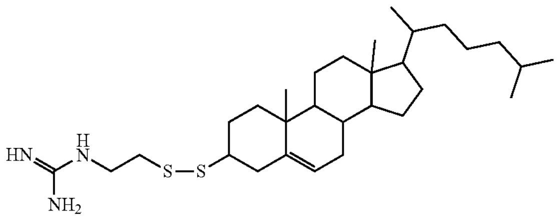

and pharmaceutically acceptable salts thereof. In certain embodiments, the compositions and methods of the present invention include a cationic lipid, “HGT4003”, having a compound structure of:

(HGT4003)

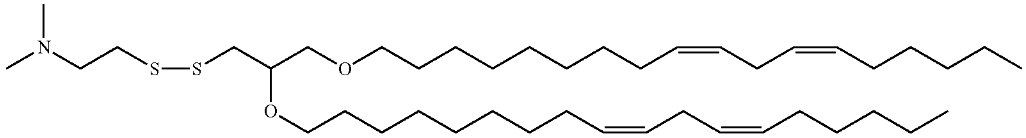

and pharmaceutically acceptable salts thereof. In certain embodiments, the compositions and methods of the present invention include a cationic lipid, “HGT4004”, having a compound structure of:

(HGT4004)

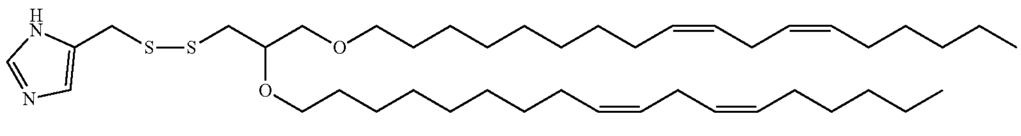

and pharmaceutically acceptable salts thereof. In certain embodiments, the compositions and methods of the present invention include a cationic lipid “HGT4005”, having a compound structure of:

(HGT4005)

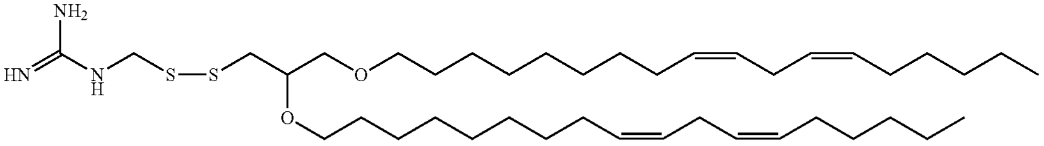

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'), (I')

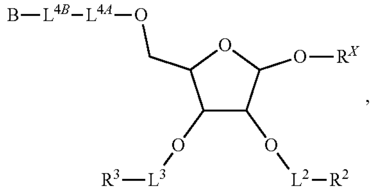

, wherein:

$R^X$ is independently —H, $-L^1-R^1$, or $-L^{5A}-L^{5B}-B'$;

each of $L^1$, $L^2$, and $L^3$ is independently a covalent bond, —C(O)—, —C(O)O—, —C(O)S—, or —C(O)$NR^L$—;

each $L^{4A}$ and $L^{5A}$ is independently —C(O)—, —C(O)O—, or —C(O)$NR^L$—;

each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is $NR^4R^5$ or a 5- to 10-membered nitrogen-containing heteroaryl;

each $R^1$, $R^2$, and $R^3$ is independently $C_6$-$C_{30}$ alkyl, $C_6$-$C_{30}$ alkenyl, or $C_6$-$C_{30}$ alkynyl; each $R^4$ and $R^5$ is independently hydrogen, $C_1$-$C_{10}$ alkyl; $C_2$-$C_{10}$ alkenyl; or $C_2$-$C_{10}$ alkynyl; and each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of 62/672,194, having a compound structure of

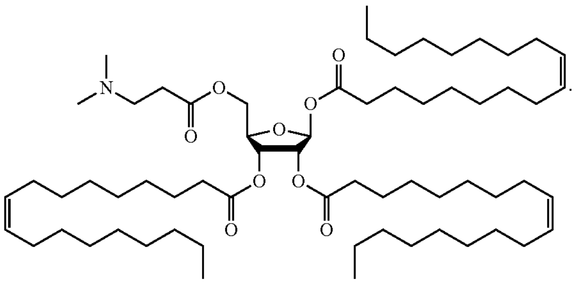

.

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido)ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9', 1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy]

octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9, 12-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)—N,N-dimethyl-2,2-di((9Z, 12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10, 13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by the following structure:

(ICE)

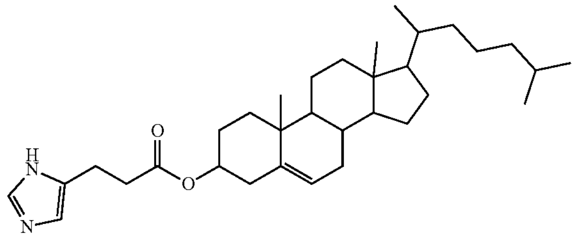

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

Non-Cationic Lipids

As used herein, the phrase "non-cationic lipid" refers to any neutral, zwitterionic or anionic lipid, which is also referred to herein as a "helper lipid". As used herein, the phrase "anionic lipid" refers to any of a number of lipid species that carry a net negative charge at a selected pH, such as physiological pH.

The invention relates to an mRNA-LNP that comprises one or more non-cationic helper lipids including 1,2-Dierucoyl-sn-glycero-3-phosphoethanolamine (DEPE). In some embodiments, DEPE is the only non-cationic helper lipid in the mRNA-LNP. In other embodiments, the helper lipid portion of the mRNA-LNP comprises DEPE and cholesterol.

Without wishing to be bound by any particular theory, certain DEPE derivatives that differ from DEPE in their lipid chain length or composition are also comprised within the invention. For example, the inventors have found that alkyl or alkene chains of 10-20 carbons in length are particular suitable for the formation of mRNA-LNPs. In some embodiments, a DEPE derivative with alkyl or alkene chains of 16-20 carbons in length is particularly preferred. Alternatively, DEPE derivatives with alkyl or alkene chains of 10-14 carbons in length, for example those with 10, 12 or 14 carbons, may be particularly suitable for the practice of the invention.

Other non-cationic lipids or helper lipids that can be included in an mRNA-LNP include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), 1-palmitoyl-2-oleoyl-sn-glycero-3-phosphoethanolamine (POPE), dioleoylphosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, a composition (e.g., a liposomal composition) comprises one or more cholesterol-based lipids. For example, a suitable cholesterol-based lipid for practicing the invention is cholesterol. Other suitable cholesterol-based lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or imidazole cholesterol ester (ICE).

In some embodiments, a cholesterol-based lipid may be present in a molar ratio (mol %) of about 1% to about 30%, or about 5% to about 20% of the total lipids present in a liposome. In some embodiments, the percentage of cholesterol-based lipid in the lipid nanoparticle may be greater than about 5 mol %, greater than about 10 mol %, greater than about 20 mol %, greater than about 30 mol %, or greater than about 40 mol %. In some embodiments, the percentage of cholesterol-based lipid in the lipid nanoparticle may be no more than about 5 mol %, no more than about 10 mol %, no more than about 20 mol %, no more than about 30 mol %, or no more than about 40 mol %.

In some embodiments, a cholesterol-based lipid may be present in a weight ratio (wt %) of about 1% to about 30%, or about 5% to about 20% of the total lipids present in a liposome. In some embodiments, the percentage of cholesterol-based lipid in the lipid nanoparticle may be greater than about 5 wt %, greater than about 10 wt %, greater than about 20 wt %, greater than about 30 wt %, or greater than about 40 wt %. In some embodiments, the percentage of cholesterol-based lipid in the lipid nanoparticle may be no more than about 5 wt %, no more than about 10 wt %, no more than about 20 wt %, no more than about 30 wt %, or no more than about 40 wt %.

PEGylated Lipids

In some embodiments, a suitable lipid solution includes one or more PEGylated lipids, also referred to herein as PEG-modified lipids. A suitable PEG-modified or PEGylated lipid for practicing the invention is 1,2-dimyristoyl-rac-glycero-3-methoxypolyethylene glycol-2000 (DMG-PEG2K). For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention. Contemplated PEG-modified lipids include, but are not limited to, a polyethylene glycol chain of up to 2 kDa, up to 3 kDa, up to 4 kDa or up to 5 kDa in length covalently attached to a lipid with alkyl chain(s) of $C_6$-$C_{20}$ length. In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$). The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., $C_{14}$ or $C_{18}$). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

PEG-modified phospholipid and derivatized lipids may constitute no greater than about 0.5%, 1%, 1.5%, 2%, 2.5%, 3%, 3.5%, 4%, 4.5% or 5% of the total lipids in a suitable lipid solution by weight or by molar. In some embodiments, PEG-modified lipids may constitute about 5% or less of the total lipids in a suitable lipid solution by weight or by molar concentration. In some embodiments, PEG-modified lipids may constitute about 4% or less of the total lipids in a suitable lipid solution by weight or by molar concentration. In some embodiments, PEG-modified lipids typically constitute 3% or less of total lipids in a suitable lipid solution by weight or by molar concentration. In some embodiments, PEG-modified lipids typically constitute 2% or less of total lipids in a suitable lipid solution by weight or by molar concentration. In some embodiments, PEG-modified lipids typically constitute 1% or less of total lipids in a suitable lipid solution by weight or by molar concentration. In some embodiments, PEG-modified lipids constitute about 1-5%, about 1-4%, about 1-3%, or about 1-2%, of the total lipids in a suitable lipid solution by weight or by molar concentration. In some embodiments, PEG modified lipids constitute about 0.01-3% (e.g., about 0.01-20.5%, 0.01-2%, 0.01-1.5%, 0.01-1%) of the total lipids in a suitable lipid solution by weight or by molar concentration.

Molar Lipid Ratios

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and tolerability of the selected lipid (s). Thus the molar ratios may be adjusted accordingly.

Various combinations of lipids, i.e., cationic lipids, non-cationic lipids, PEG-modified lipids and optionally cholesterol, that can used to prepare, and that are comprised in, preformed lipid nanoparticles are described in the literature and herein. For example, a suitable lipid solution may contain cKK-E12, DEPE, cholesterol, and DMG-PEG2K; C12-200, DEPE, cholesterol, and DMG-PEG2K; HGT5000, DEPE, cholesterol, and DMG-PEG2K; HGT5001, DEPE, cholesterol, and DMG-PEG2K; cKK-E12, DPPC, cholesterol, and DMG-PEG2K; C12-200, DPPC, cholesterol, and DMG-PEG2K; HGT5000, DPPC, chol, and DMG-PEG2K; HGT5001, DPPC, cholesterol, and DMG-PEG2K; or ICE, DEPE and DMG-PEG2K. Additional combinations of lipids are described in the art, e.g., PCT/US17/61100, filed on Nov. 10, 2017, published as WO 2018/089790; entitled "Novel ICE-based Lipid Nanoparticle Formulation for Delivery of mRNA,"; PCT/US18/21292, filed on Mar. 7, 2018, published as WO 2018/165257, entitled "PolyAnionic Delivery of Nucleic Acids"; PCT/US18/36920, filed on Jun. 11, 2018, entitled, "Poly (Phosphoesters) for Delivery of Nucleic Acids"; U.S. Provisional Application 62/676,147, filed on May 24, 2018; entitled "Thioester Cationic Lipids"; U.S. Provisional Application 62/677,821, filed on May 30, 2018 entitled "Cationic Lipids Comprising a Steroidal Moiety"; U.S. Provisional Application 62/677,809, filed on May 30, 2018, entitled "Macrocyclic Lipids"; U.S. Provisional Application 62/677,818, filed on May 30, 2018, entitled "Vitamin K Cationic Lipids"; U.S. Provisional Application 62/677,828, filed on May 30, 2018, entitled "Vitamin D Cationic Lipids"; U.S. Provisional Application 62/677,851, filed on May 30, 2018, entitled "Vitamin A Cationic Lipids"; U.S. Provisional Application 62/677,855, filed on May 30, 2018, entitled "Vitamin E Cationic Lipids"; the disclosures of which are included here in their full scope by reference.

In various embodiments, cationic lipids (e.g., cKK-E12, Compound 1, Compound 2, or Compound 3, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, Compound 1, Compound 2, or Compound 3, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5. In some embodiments, the ratio of sterol lipid(s) to non-cationic lipid(s) to PEG-modified lipid(s) is 50:45:5. In some embodiments, the ratio of sterol lipid(s) to non-cationic lipid(s) to PEG-modified lipid(s) is 50:40:10. In some embodiments, the ratio of sterol lipid(s) to non-cationic lipid(s) to PEG-modified lipid(s) is 55:40:5. In some embodiments, the ratio of sterol lipid(s) to non-cationic lipid(s) to PEG-modified lipid(s) is 55:35:10. In some embodiments, the ratio of sterol lipid(s) to non-cationic lipid(s) to PEG-modified lipid(s) is 60:35:5. In some embodiments, the ratio of sterol lipid(s) to non-cationic lipid(s) to PEG-modified lipid(s) is 60:30:10.

In some embodiments, a suitable liposome for the present invention comprises ICE and DEPE at an ICE:DEPE molar ratio of >1:1. In some embodiments, the ICE:DEPE molar ratio is <2.5:1. In some embodiments, the ICE:DEPE molar ratio is between 1:1 and 2.5:1. In some embodiments, the ICE:DEPE molar ratio is approximately 1.5:1. In some embodiments, the ICE:DEPE molar ratio is approximately 1.7:1. In some embodiments, the ICE:DEPE molar ratio is approximately 2:1. In some embodiments, a suitable liposome for the present invention comprises ICE and DMG-PEG-2K at an ICE:DMG-PEG-2K molar ratio of >10:1. In some embodiments, the ICE:DMG-PEG-2K molar ratio is <16:1. In some embodiments, the ICE:DMG-PEG-2K molar ratio is approximately 12:1. In some embodiments, the ICE:DMG-PEG-2K molar ratio is approximately 14:1. In some embodiments, a suitable liposome for the present invention comprises DEPE and DMG-PEG-2K at a DEPE:DMG-PEG-2K molar ratio of >5:1. In some embodiments, the DEPE:DMG-PEG-2K molar ratio is <11:1. In some embodiments, the DEPE:DMG-PEG-2K molar ratio is approximately 7:1. In some embodiments, the DEPE:DMG-PEG-2K molar ratio is approximately 10:1.

In some embodiments, a suitable liposome for the present invention comprises ICE, DEPE and DMG-PEG-2K at an ICE:DEPE:DMG-PEG-2K molar ratio of 50:45:5. In some embodiments, a suitable liposome for the present invention comprises ICE, DEPE and DMG-PEG-2K at an ICE:DEPE:DMG-PEG-2K molar ratio of 50:40:10. In some embodiments, a suitable liposome for the present invention comprises ICE, DEPE and DMG-PEG-2K at an ICE:DEPE:DMG-PEG-2K molar ratio of 55:40:5. In some embodiments, a suitable liposome for the present invention comprises ICE, DEPE and DMG-PEG-2K at an ICE:DEPE:DMG-PEG-2K molar ratio of 55:35:10. In some embodiments, a suitable liposome for the present invention comprises ICE, DEPE and DMG-PEG-2K at an ICE:DEPE:DMG-PEG-2K molar ratio of 60:35:5. In some embodiments, a suitable liposome for the present invention comprises ICE, DEPE and DMG-PEG-2K at an ICE:DEPE:DMG-PEG-2K molar ratio of 60:30:10.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

Messenger RNA (mRNA)

The present invention may be used to encapsulate any mRNA. mRNA is typically thought of as the type of RNA that carries information from DNA to the ribosome. Typically, in eukaryotic organisms, mRNA processing comprises the addition of a "cap" on the 5' end, and a "tail" on the 3' end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The additional of a tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

mRNAs may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNase I, pyrophosphatase, and/or RNAse inhibitor. The exact conditions will vary according to the specific application.

In some embodiments, in vitro synthesized mRNA may be purified before formulation and encapsulation to remove undesirable impurities including various enzymes and other reagents used during mRNA synthesis.

The present invention may be used to formulate and encapsulate mRNAs of a variety of lengths. In some embodiments, the present invention may be used to formulate and encapsulate in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to formulate and encapsulate in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

The present invention may be used to formulate and encapsulate mRNA that is unmodified or mRNA containing one or more modifications that typically enhance stability. In some embodiments, modifications are selected from modified nucleotides, modified sugar phosphate backbones, and 5' and/or 3' untranslated region.

In some embodiments, modifications of mRNA may include modifications of the nucleotides of the RNA. A modified mRNA according to the invention can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydrouracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine, pseudouridine, 5-methylcytidine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA and m7GpppNmpNmp-RNA (where m indicates 2'-Omethyl residues).

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

While mRNA provided from in vitro transcription reactions may be desirable in some embodiments, other sources of mRNA are contemplated as within the scope of the invention including mRNA produced from bacteria, fungi, plants, and/or animals.

The present invention may be used to formulate and encapsulate mRNAs encoding a variety of proteins. Non-limiting examples of mRNAs suitable for the present invention include mRNAs encoding spinal motor neuron 1 (SMN), alpha-galactosidase (GLA), argininosuccinate synthetase (ASS1), omithine transcarbamylase (OTC), Factor IX (FIX), phenylalanine hydroxylase (PAH), erythropoietin (EPO), cystic fibrosis transmembrane conductance receptor (CFTR) and firefly luciferase (FFL).

Formation of Lipid Nanoparticles (LNPs)

Also provided is a method for preparing a lipid nanoparticle encapsulating a mRNA, said method comprising (a) providing a mixture of one or more cationic lipids, one or more PEG-modified lipids and one or more helper lipids, wherein the one or more helper lipids comprises 1,2-Dierucoyl-sn-glycero-3-phosphoethanolamine (DEPE), and (b) forming a lipid nanoparticle form the mixture provided in step (a), wherein the method further comprises encapsulating the mRNA into the lipid nanoparticle, wherein encapsulation can take place before or after formation of the lipid nanoparticle in step (b). The resulting lipid nanoparticle encapsulating the mRNA is stable (e.g., maintains the same encapsulation of mRNA before and after freeze-thaw, or maintains within 10% of the same encapsulation of mRNA before and after freeze thaw). In one embodiment, the method for preparing a lipid nanoparticle in accordance with the invention specifically excludes the use of one or more helper lipids selected from dioleoylphosphatidylethanolamine (DOPE), 1,2-Dilinoleoyl-sn-glycero-3-phosphoethanolamine (DLOPE), 1-palmitoyl-2-oleoyl-sn-glycero-3-phosphoethanolamine (POPE), and combinations thereof.

Various encapsulation processes are described in published U.S. Application No. US 2011/0244026, published U.S. Application No. US 2016/0038432, published U.S. Application No. US 2018/0153822, published U.S. Application No. US 2018/0125989 and U.S. Provisional Application No. 62/877,597, filed Jul. 23, 2019 and can be used to practice the present invention, all of which are incorporated herein by reference. As used herein, Process A refers to a conventional method of encapsulating mRNA by mixing mRNA with a mixture of lipids, without first pre-forming the lipids into lipid nanoparticles, as described in US 2016/0038432. As used herein, Process B or "Remix" refers to a process of encapsulating messenger RNA (mRNA) by mixing pre-formed lipid nanoparticles with mRNA, as described in US 2018/0153822. "Step Down Remix" or "Step Up Remix" are improved processes that builds on the "Remix" process, as described in U.S. Provisional Application 63/021,319. "Step Down Remix" involves mixing a suspension of preformed empty lipid nanoparticles, with batches of a solution of mRNA that are added sequentially. Each addition of mRNA solution batch results in an intermediate mixture with a different molar ratio of cationic lipid to mRNA ("N/P"), starting with a high N/P ratio, and decrease to a lower N/P ratio in the final formulation. In "Step Up Remix", a suspension of preformed empty lipid nanoparticles is added in batches to an mRNA solution, starting with an equimolar ratio of cationic lipid to mRNA. For example, four batches of preformed empty lipid nanoparticles are added until a ratio of 4 (cationic lipid) to 1 (mRNA) is reached.

In one embodiment, the DEPE is present in the mixture at a concentration of between 10 molar percent and 50 molar percent. More typically, the DEPE in the mixture is present at a concentration of between 25 molar present and 35 molar percent of the total lipids in the mixture. In one embodiment, the one or more PEG-modified lipids in the mixture comprises a poly(ethylene) glycol chain of up to 5 kDa in length covalently attached to a lipid with alkyl chain(s) of $C_6$-$C_{20}$ length. In one embodiment, the mixture one or more cationic lipids, one or more PEG-modified lipids and one or more helper lipids further comprises one or more sterols, such as a cholesterol-based lipid. In one embodiment, a cholesterol-based lipid is cholesterol and/or PEGylated cholesterol. In some embodiments, the ratio of cationic lipid(s) to helper lipid(s) to cholesterol-based lipid(s) to PEG-modified lipid (s) may be between about 30-60:25-35:20-30:1-15, respectively.

In some embodiments, the empty preformed lipid nanoparticles are formed by mixing lipids dissolved in ethanol with an aqueous solution (Lipid Solution). In some embodiments, the lipids contain one or more cationic lipids, one or more non-cationic lipids, and one or more PEG lipids. In some embodiments, the lipids also contain one or more cholesterol lipids. In some embodiments, the lipids are present in ethanolic stock solution. The preformed lipid nanoparticles are formed by the mixing of those lipids. Typically, in some embodiments, a lipid solution containing dissolved lipids, and an aqueous or buffer solution are mixed into a solution such that the lipids can form nanoparticles without mRNA (i.e., empty preformed lipid nanoparticles).

Lipid Solution

According to the present invention, a lipid solution contains a mixture of lipids suitable to form lipid nanoparticles for encapsulation of mRNA. In some embodiments, a suitable lipid solution is ethanol based. For example, a suitable lipid solution may contain a mixture of desired lipids dissolved in pure ethanol (i.e., 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. For example, a suitable lipid solution may contain a mixture of desired lipids at a total concentration of about 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 30 mg/ml, 40 mg/ml, 50 mg/ml, or 100 mg/ml. In some embodiments, a suitable lipid solution may contain a mixture of desired lipids at a total concentration ranging from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml. In some embodiments, a suitable lipid solution may contain a mixture of desired lipids at a total concentration up to about 100 mg/ml, 90 mg/ml, 80 mg/ml, 70 mg/ml, 60 mg/ml, 50 mg/ml, 40 mg/ml, 30 mg/ml, 20 mg/ml, or 10 mg/ml.

Any desired lipids may be mixed at any ratios suitable for encapsulating mRNAs. In some embodiments, a suitable lipid solution contains a mixture of desired lipids including cationic lipids, helper lipids (e.g. non cationic lipids and/or cholesterol lipids) and/or PEGylated lipids. In some embodiments, a suitable lipid solution contains a mixture of desired lipids including one or more cationic lipids, one or more helper lipids (e.g. non cationic lipids and/or cholesterol lipids) and one or more PEGylated lipids. In some embodiments, a suitable lipid solution contains a mixture of desired lipids including one or more neutral lipids, one or more helper lipids and one or more PEGylated lipids.

In some embodiments, an empty (i.e., absence of mRNA) preformed lipid nanoparticle formulation used in making nanoparticle formulation of the invention can be stably frozen in about 5%, about 10%, about 15%, about 20%, about 25%, about 30%, about 35%, about 40%, about 45%, or about 50% trehalose solution. In some embodiments, addition of mRNA to empty lipid nanoparticles can result in a final formulation that does not require any downstream purification or processing and can be stably stored in frozen form.

Formation of mRNA-LNPs

As used herein, a process for formation of mRNA-loaded lipid nanoparticles (mRNA-LNPs) is used interchangeably with the term "mRNA encapsulation" or grammatical variants thereof. In some embodiments, mRNA-LNPs are formed by mixing an mRNA solution with a lipid solution, wherein the mRNA solution and/or the lipid solution are heated to a pre-determined temperature greater than ambient temperature prior to mixing (see U.S. patent application Ser. No. 14/790,562 entitled "Encapsulation of messenger RNA", filed Jul. 2, 2015 and its provisional U.S. patent application Ser. No. 62/020,163, filed Jul. 2, 2014, the disclosure of which are hereby incorporated in their entirety).

Typically, any desired lipids may be mixed at any ratios suitable for formation of the mRNA-LNPs. In some embodiments, a suitable lipid solution contains a mixture of desired lipids including cationic lipids, helper lipids (e.g. non cationic lipids and/or cholesterol lipids) and/or PEGylated lipids. In some embodiments, a suitable lipid solution contains a mixture of desired lipids including one or more cationic lipids, one or more helper lipids (e.g. non cationic lipids and/or cholesterol lipids) and one or more PEGylated lipids. In some embodiments, a suitable lipid solution contains a mixture of desired lipids including one or more neutral lipids, one or more helper lipids and one or more PEGylated lipids.

In some embodiments, an mRNA solution and a preformed lipid nanoparticle solution are mixed into a solution such that the mRNA becomes encapsulated in the lipid nanoparticle. Such a solution is also referred to as a formulation or encapsulation solution. A process for encapsulating mRNA by mixing preformed lipid nanoparticles with mRNA has been previously described in an earlier invention filed as PCT/US17/61113 on Nov. 10, 2017, which published as WO2018/089801; and concurrently filed U.S. patent application Ser. No. 15/809,68, both are entitled “Improved Process of Preparing mRNA-Loaded Lipid Nanoparticles”. The entire content of the application is hereby incorporated by reference.

A suitable formulation or encapsulation solution includes a solvent such as ethanol. For example, a suitable formulation or encapsulation solution includes about 10% ethanol, about 15% ethanol, about 20% ethanol, about 25% ethanol, about 30% ethanol, about 35% ethanol, or about 40% ethanol. In some embodiments, a suitable formulation or encapsulation solution includes a solvent such as isopropyl alcohol. For example, a suitable formulation or encapsulation solution includes about 10% isopropyl alcohol, about 15% isopropyl alcohol, about 20% isopropyl alcohol, about 25% isopropyl alcohol, about 30% isopropyl alcohol, about 35% isopropyl alcohol, or about 40% isopropyl alcohol.

In some embodiments, a suitable formulation or encapsulation solution includes a solvent such as dimethyl sulfoxide. For example, a suitable formulation or encapsulation solution includes about 10% dimethyl sulfoxide, about 15% dimethyl sulfoxide, about 20% dimethyl sulfoxide, about 25% dimethyl sulfoxide, about 30% dimethyl sulfoxide, about 35% dimethyl sulfoxide, or about 40% dimethyl sulfoxide.

In some embodiments, a suitable formulation or encapsulation solution may also contain a buffering agent or salt. Exemplary buffering agent may include HEPES, ammonium sulfate, sodium bicarbonate, sodium citrate, sodium acetate, potassium phosphate and sodium phosphate. Exemplary salt may include sodium chloride, magnesium chloride, and potassium chloride. In some embodiments, an empty preformed lipid nanoparticle formulation used in making this novel nanoparticle formulation can be stably frozen in 10% trehalose solution.

In some embodiments, ethanol, citrate buffer, and other destabilizing agents are absent during the addition of mRNA and hence the formulation does not require any further downstream processing. In some embodiments, the lipid nanoparticle formulation prepared by this novel process comprises preformed lipid nanoparticles in trehalose solution. The lack of destabilizing agents and the stability of trehalose solution increase the ease of scaling up the formulation and production of mRNA-encapsulated lipid nanoparticles.

mRNA Solution mRNA may be provided in a solution to be mixed with a lipid solution such that the mRNA may be encapsulated in lipid nanoparticles. A suitable mRNA solution may be any aqueous solution containing mRNA to be encapsulated at various concentrations below 1 mg/ml. For example, a suitable mRNA solution may contain an mRNA at a concentration of or less than about 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in an mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Various methods may be used to prepare an mRNA solution suitable for the present invention. In some embodiments, mRNA may be directly dissolved in a buffer solution described herein. In some embodiments, an mRNA solution may be generated by mixing an mRNA stock solution with a buffer solution prior to mixing with a lipid solution for encapsulation. In some embodiments, an mRNA solution may be generated by mixing an mRNA stock solution with a buffer solution immediately before mixing with a lipid solution for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffer solution using a pump. Exemplary pumps include but are not limited to gear pumps, peristaltic pumps and centrifugal pumps.

Typically, the buffer solution is mixed at a rate greater than that of the mRNA stock solution. For example, the buffer solution may be mixed at a rate at least 1×, 2×, 3×, 4×, 5×, 6×, 7×, 8×, 9×, 10×, 15×, or 20× greater than the rate of the mRNA stock solution. In some embodiments, a process according to the present invention includes a step of first generating an mRNA solution by mixing a citrate buffer with an mRNA stock solution. In certain embodiments, a suitable citrate buffer contains about 10 mM citrate, about 150 mM NaCl, pH of about 4.5. In some embodiments, a suitable mRNA stock solution contains the mRNA at a concentration at or greater than about 1 mg/ml, about 10 mg/ml, about 50 mg/ml, or about 100 mg/ml.

In some embodiments, the citrate buffer is mixed at a flow rate ranging between about 100-300 ml/minute, 300-600 ml/minute, 600-1200 ml/minute, 1200-2400 ml/minute, 2400-3600 ml/minute, 3600-4800 ml/minute, or 4800-6000 ml/minute. In some embodiments, the citrate buffer is mixed at a flow rate of about 220 ml/minute, about 600 ml/minute, about 1200 ml/minute, about 2400 ml/minute, about 3600 ml/minute, about 4800 ml/minute, or about 6000 ml/minute.

In some embodiments, the mRNA stock solution is mixed at a flow rate ranging between about 10-30 ml/minute, about 30-60 ml/minute, about 60-120 ml/minute, about 120-240 ml/minute, about 240-360 ml/minute, about 360-480 ml/minute, or about 480-600 ml/minute. In some embodiments, the mRNA stock solution is mixed at a flow rate of about 20 ml/minute, about 40 ml/minute, about 60 ml/minute, about 80 ml/minute, about 100 ml/minute, about 200 ml/minute, about 300 ml/minute, about 400 ml/minute, about 500 ml/minute, or about 600 ml/minute.

In some embodiments, a buffer solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffer solution is mixed at a flow rate of or greater than about 60 ml/minute, 100 ml/minute, 140 ml/minute, 180 ml/minute, 220 ml/minute, 260 ml/minute, 300 ml/minute, 340 ml/minute, 380 ml/minute, 420 ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, an mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, an mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

In some embodiments, the preformed lipid nanoparticles and mRNA are mixed using a pump system. In some embodiments, the pump system comprises a pulse-less flow pump. In some embodiments, the pump system is a gear pump. In some embodiments, a suitable pump is a peristaltic pump. In some embodiments, a suitable pump is a centrifugal pump. In some embodiments, the process using a pump system is performed at large scale. For example, in some embodiments, the process includes using pumps as described herein to mix a solution of at least about 1 mg, 5 mg, 10 mg, 50 mg, 100 mg, 500 mg, or 1000 mg of mRNA with a solution of pre-formed lipid nanoparticles, to produce mRNA encapsulated in lipid nanoparticles. In some embodiments, the process of mixing mRNA with preformed lipid nanoparticles provides a composition according to the present invention that contains at least about 1 mg, 5 mg, 10 mg, 50 mg, 100 mg, 500 mg, or 1000 mg of encapsulated mRNA.

In some embodiments, the solution comprising preformed lipid nanoparticles is mixed at a flow rate ranging from about 25-75 ml/minute, about 75-200 ml/minute, about 200-350 ml/minute, about 350-500 ml/minute, about 500-650 ml/minute, about 650-850 ml/minute, or about 850-1000 ml/minute. In some embodiments, the solution comprising preformed lipid nanoparticles is mixed at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, the mRNA is mixed in a solution at a flow rate ranging from about 25-75 ml/minute, about 75-200 ml/minute, about 200-350 ml/minute, about 350-500 ml/minute, about 500-650 ml/minute, about 650-850 ml/minute, or about 850-1000 ml/minute. In some embodiments, the mRNA is mixed in a solution at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, a step of combining lipid nanoparticles encapsulating mRNA with preformed lipid particles is performed using a pump system. Such combining may be performed using a pump. In some embodiments, the mRNA-encapsulated lipid nanoparticles are mixed with preformed lipid nanoparticles are mixed at a flow rate ranging from about 25-75 ml/minute, about 75-200 ml/minute, about 200-350 ml/minute, about 350-500 ml/minute, about 500-650 ml/minute, about 650-850 ml/minute, or about 850-1000 ml/minute. In some embodiments, the mRNA is mixed in a solution at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, the mixing of lipid nanoparticles and mRNA is performed in absence of any pump.

In some embodiments, the process according to the present invention includes a step of heating one or more of the solutions (i.e., applying heat from a heat source to the solution) to a temperature (or to maintain at a temperature) greater than ambient temperature, the one more solutions being the solution comprising the preformed lipid nanoparticles, the solution comprising the mRNA and the mixed solution comprising the lipid nanoparticle encapsulated mRNA. In some embodiments, the process includes the step of heating one or both of the mRNA solution and the preformed lipid nanoparticle solution, prior to the mixing step. In some embodiments, the process includes heating one or more one or more of the solutions comprising the preformed lipid nanoparticles, the solution comprising the mRNA and the solution comprising the lipid nanoparticle encapsulated mRNA, during the mixing step. In some embodiments, the process includes the step of heating the lipid nanoparticle encapsulated mRNA, after the mixing step. In some embodiments, the temperature to which one or more of the solutions is heated (or at which one or more of the solutions is maintained) is or is greater than about 30° C., 37° C., 40° C., 45° C., 50° C., 55° C., 60° C., 65° C., or 70° C. In some embodiments, the temperature to which one or more of the solutions is heated ranges from about 25-70° C., about 30-70° C., about 35-70° C., about 40-70° C., about 45-70° C., about 50-70° C., or about 60-70° C. In some embodiments, the temperature greater than ambient temperature to which one or more of the solutions is heated is about 65° C.

In some embodiments, the process according to the present invention includes maintaining at ambient temperature (i.e., not applying heat from a heat source to the solution) one or more of the solutions comprising the preformed lipid nanoparticles, the solution comprising the mRNA and the mixed solution comprising the lipid nanoparticle encapsulated mRNA. In some embodiments, the process includes the step of maintaining at ambient temperature one or both of the mRNA solution and the preformed lipid nanoparticle solution, prior to the mixing step. In some embodiments, the process includes maintaining at ambient temperature one or more one or more of the solutions comprising the preformed lipid nanoparticles, the solution comprising the mRNA and the solution comprising the lipid nanoparticle encapsulated mRNA, during the mixing step. In some embodiments, the process includes the step of maintaining the lipid nanoparticle encapsulated mRNA at ambient temperature after the mixing step. In some embodiments, the ambient temperature at which one or more of the solutions is maintained is or is less than about 35° C., 30° C., 25° C., 20° C., or 16° C. In some embodiments, the ambient temperature at which one or more of the solutions is maintained ranges from about 15-35° C., about 15-30° C., about 15-25° C., about 15-20° C., about 20-35° C., about 25-35° C., about 30-35° C., about 20-30° C., about 25-30° C. or about 20-25° C. In some embodiments, the ambient temperature at which one or more of the solutions is maintained is 20-25° C.

In some embodiments, the process according to the present invention includes performing at ambient temperature the step of mixing the solution comprising preformed lipid nanoparticles and the solution comprising mRNA to form lipid nanoparticles encapsulating mRNA.

In some embodiments, greater than about 50%, 55%, 60%, 65%, 70%, 75%, 80%, 85%, 90%, 95%, 96%, 97%, 98%, or 99% of the purified nanoparticles have a size less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, substantially all of the purified nanoparticles have a size less than 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, greater than about 70%, 75%, 80%, 85%, 90%, 95%, 96%, 97%, 98%, 99% of the purified nanoparticles have a size ranging from 50-150 nm. In some embodiments, substantially all of the purified nanoparticles have a size ranging from 50-150 nm. In some embodiments, greater than about 70%, 75%, 80%, 85%, 90%, 95%, 96%, 97%, 98%, 99% of the purified nanoparticles have a size ranging from 80-150 nm. In some embodiments, substantially all of the purified nanoparticles have a size ranging from 80-150 nm.

In some embodiments, a process according to the present invention results in an encapsulation rate of greater than about 90%, 95%, 96%, 97%, 98%, or 99%. In some embodiments, a process according to the present invention results in greater than about 60%, 65%, 70%, 75%, 80%, 85%, 90%, 95%, 96%, 97%, 98%, or 99% recovery of mRNA.

In some embodiments, lipid nanoparticles encapsulating mRNA are combined with preformed lipid particles in step (b) of the process at a ratio of 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, or 1:20. The process of combining the lipid nanoparticles are as described above for mixing lipid nanoparticles with mRNA. In some embodiments, lipid nanoparticles encapsulating mRNA are combined with preformed lipid particles in step (b) of the process at a ratio of 20:1. In some embodiments, lipid nanoparticles encapsulating mRNA are combined with preformed lipid particles in step (b) of the process at a ratio of 19:1. In some embodiments, lipid nanoparticles encapsulating mRNA are combined with preformed lipid particles in step (b) of the process at a ratio of 15:1. In some embodiments, lipid nanoparticles encapsulating mRNA are combined with preformed lipid particles in step (b) of the process at a ratio of 10:1. In some embodiments, lipid nanoparticles encapsulating mRNA are combined with preformed lipid particles in step (b) of the process at a ratio of 9:1. In some embodiments, lipid nanoparticles encapsulating mRNA are combined with preformed lipid particles in step (b) of the process at a ratio of 8:1. In some embodiments, lipid nanoparticles encapsulating mRNA are combined with preformed lipid particles in step (b) of the process at a ratio of 7:1. In some embodiments, lipid nanoparticles encapsulating mRNA are combined with preformed lipid particles in step (b) of the process at a ratio of 6:1. In some embodiments, lipid nanoparticles encapsulating mRNA are combined with preformed lipid particles in step (b) of the process at a ratio of 5:1. In some embodiments, lipid nanoparticles encapsulating mRNA are combined with preformed lipid particles in step (b) of the process at a ratio of 4:1. In some embodiments, lipid nanoparticles encapsulating mRNA are combined with preformed lipid particles in step (b) of the process at a ratio of 3:1. In some embodiments, lipid nanoparticles encapsulating mRNA are combined with preformed lipid particles in step (b) of the process at a ratio of 2:1. In some embodiments, lipid nanoparticles encapsulating mRNA are combined with preformed lipid particles in step (b) of the process at a ratio of 1:1. In some embodiments, lipid nanoparticles encapsulating mRNA are combined with preformed lipid particles in step (b) of the process at a ratio of 1:2. In some embodiments, lipid nanoparticles encapsulating mRNA are combined with preformed lipid particles in step (b) of the process at a ratio of 1:3. In some embodiments, lipid nanoparticles encapsulating mRNA are combined with preformed lipid particles in step (b) of the process at a ratio of 1:4. In some embodiments, lipid nanoparticles encapsulating mRNA are combined with preformed lipid particles in step (b) of the process at a ratio of 1:5. In some embodiments, lipid nanoparticles encapsulating mRNA are combined with preformed lipid particles in step (b) of the process at a ratio of 1:6. In some embodiments, lipid nanoparticles encapsulating mRNA are combined with preformed lipid particles in step (b) of the process at a ratio of 1:7. In some embodiments, lipid nanoparticles encapsulating mRNA are combined with preformed lipid particles in step (b) of the process at a ratio of 1:8. In some embodiments, lipid nanoparticles encapsulating mRNA are combined with preformed lipid particles in step (b) of the process at a ratio of 1:9. In some embodiments, lipid nanoparticles encapsulating mRNA are combined with preformed lipid particles in step (b) of the process at a ratio of 1:10. In some embodiments, lipid nanoparticles encapsulating mRNA are combined with preformed lipid particles in step (b) of the process at a ratio of 1:12. In some embodiments, lipid nanoparticles encapsulating mRNA are combined with preformed lipid particles in step (b) of the process at a ratio of 1:15. In some embodiments, lipid nanoparticles encapsulating mRNA are combined with preformed lipid particles in step (b) of the process at a ratio of 1:20.

Purification

In some embodiments, the empty preformed lipid nanoparticles or mRNA-LNPs are purified and/or concentrated. Various purification methods may be used. In some embodiments, the lipid nanoparticles are purified by a Tangential Flow Filtration (TFF) process. In some embodiments, the lipid nanoparticles are purified by gravity-based normal flow filtration (NFF). In some embodiments, the lipid nanoparticles are purified by any other suitable filtration process. In some embodiments, the lipid nanoparticles are purified by centrifugation. In some embodiments, the lipid nanoparticles are purified by chromatographic methods.

Pharmaceutical Formulation and Therapeutic Uses

The composition comprising mRNA-LNPs may be formulated in a desired buffer such as, for example, PBS.

A process according to the present invention results in mRNA-LNP composition of higher potency and efficacy thereby allowing for lower doses thereby shifting the therapeutic index in a positive direction. In some embodiments, the process according to the present invention results in homogeneous mRNA-LNPs having small particle sizes (e.g., less than 150 nm).

Thus, the present invention provides a composition comprising mRNA-LNPs described herein. In some embodiments, majority of purified nanoparticles in a composition, i.e., greater than about 50%, 55%, 60%, 65%, 70%, 75%, 80%, 85%, 90%, 95%, 96%, 97%, 98%, or 99% of the purified nanoparticles, have a size of less than about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, substantially all of the mRNA-LNPs have a size of less than about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). Lipid nanoparticles having a size of less than 100 nm are particularly suitable because they can penetrate through the liver fenestration and gain access to hepatocytes. Similarly, lipid nanoparticles having a size of about 100 nm or less are readily nebulized and can penetrate deep into the lung when administered to a subject using nebulization.

In addition, more homogeneous nanoparticles with narrow particle size range are achieved by a process of the present invention. For example, greater than about 70%, 75%, 80%, 85%, 90%, 95%, 96%, 97%, 98%, 99% of the nanoparticles in a composition provided by the present invention have a size ranging from about 75-150 nm (e.g., about 75-145 nm, about 75-140 nm, about 75-135 nm, about 75-130 nm, about 75-125 nm, about 75-120 nm, about 75-115 nm, about 75-110 nm, about 75-105 nm, about 75-100 nm, about 75-95 nm, about 75-90 nm, or 75-85 nm). In some embodiments, substantially all of the purified nanoparticles have a size ranging from about 75-150 nm (e.g., about 75-145 nm, about 75-140 nm, about 75-135 nm, about 75-130 nm, about 75-125 nm, about 75-120 nm, about 75-115 nm, about 75-110 nm, about 75-105 nm, about 75-100 nm, about 75-95 nm, about 75-90 nm, or 75-85 nm).

In some embodiments, the dispersity, or measure of heterogeneity in size of molecules (PDI), of nanoparticles in a composition provided by the present invention is less than about 0.23 (e.g., less than about 0.23, 0.22, 0.21, 0.20, 0.19, 0.18, 0.17, 0.16, 0.15, 0.14, 0.13, 0.12, 0.11, 0.10, 0.09, or 0.08). In a particular embodiment, the PDI is less than about 0.16.

In some embodiments, a composition according to the present invention contains at least about 1 mg, 5 mg, 10 mg, 100 mg, 500 mg, or 1000 mg of encapsulated mRNA. In some embodiments, a process according to the present invention results in greater than about 60%, 65%, 70%, 75%, 80%, 85%, 90%, 95%, 96%, 97%, 98%, or 99% recovery of mRNA.

In some embodiments, the mRNA in the composition of the invention retains an integrity of greater than 80%, 85%, 90%, 95%, 96%, 97%, 98% or 99%. In some embodiments the mRNA has an integrity of 100%.

In some embodiments, a composition according to the present invention is formulated so as to administer specific doses of the composition to a subject. In some embodiments, a composition of mRNA lipid nanoparticles as described herein is formulated at a dose concentration of about 5 mg/kg mRNA or less than 5 mg/kg mRNA, (i.e., less than 4 mg/kg mRNA, less than 3 mg/kg, less than 2 mg/kg, 1.0 mg/kg 0.6 mg/kg, 0.5 mg/kg, 0.3 mg/kg, 0.016 mg/kg. 0.05 mg/kg, and 0.016 mg/kg of mRNA). In some embodiments, the composition of mRNA lipid nanoparticles as described herein is formulated at a dose concentration of less than 4 mg/kg mRNA lipid nanoparticles. In some embodiments, the composition of mRNA lipid nanoparticles as described herein is formulated at a dose concentration of less than 3 mg/kg mRNA lipid nanoparticles. In some embodiments, the composition of mRNA lipid nanoparticles as described herein is formulated at a dose concentration of less than 2 mg/kg mRNA lipid nanoparticles. In some embodiments, the composition of mRNA lipid nanoparticles as described herein is formulated at a dose concentration of less than 1 mg/kg mRNA lipid nanoparticles. In some embodiments, the composition of mRNA lipid nanoparticles as described herein is formulated at a dose concentration of less than 0.6 mg/kg mRNA lipid nanoparticles. In some embodiments, the composition of mRNA lipid nanoparticles as described herein is formulated at a dose concentration of less than 0.5 mg/kg mRNA lipid nanoparticles. In some embodiments, the composition of mRNA lipid nanoparticles as described herein is formulated at a dose concentration of less than 0.3 mg/kg mRNA lipid nanoparticles. In some embodiments, the composition of mRNA lipid nanoparticles as described herein is formulated at a dose concentration of less than 0.2 mg/kg mRNA lipid nanoparticles. In some embodiments, the composition of mRNA lipid nanoparticles as described herein is formulated at a dose concentration of less than 0.1 mg/kg mRNA lipid nanoparticles. In some embodiments, the composition of mRNA lipid nanoparticles as described herein is formulated at a dose concentration of less than 0.0.08 mg/kg mRNA lipid nanoparticles. In some embodiments, the composition of mRNA lipid nanoparticles as described herein is formulated at a dose concentration of less than 0.06 mg/kg mRNA lipid nanoparticles. In some embodiments, the composition of mRNA lipid nanoparticles as described herein is formulated at a dose concentration of less than 0. 0.05 mg/kg mRNA lipid nanoparticles. In some embodiments, the composition of mRNA lipid nanoparticles as described herein is formulated at a dose concentration of less than 0.01 mg/kg mRNA lipid nanoparticles.

In certain embodiments, the amount of mRNA required to effectuate a therapeutic effect is reduced by at least about 10%, 15%, 20%, 25%, 30%, 40%, 50%, 60%, 75%, 80%, 90%, 95% or 99%. In certain embodiments, the amount of a polynucleotide required to effectuate a therapeutic effect is reduced by at least two-, three-, four-, five-, six-, seven-, eight- nine- ten-, twelve-, fifteen-, twenty- or twenty-five-fold or more.

Accordingly, in certain embodiments the present invention provides a method for producing a therapeutic composition comprising purified mRNA that encodes a peptide or polypeptide for use in the delivery to or treatment of a human subject. In some embodiments, therapeutic composition comprising purified mRNA is used for delivery in the lung of a subject or a lung cell. In certain embodiments, the present invention provides a method for producing a therapeutic composition comprising purified mRNA that encodes an endogenous protein which may be deficient or non-functional in a subject. In certain embodiments, the present invention provides a method for producing a therapeutic composition comprising purified mRNA that encodes an endogenous protein which may be deficient or non-functional in a subject.

In certain embodiments, the present invention provides a method for producing a therapeutic composition comprising purified mRNA that encodes a peptide or polypeptide for use in the delivery to or treatment of the lung of a subject or a lung cell. In certain embodiments the present invention is useful in a method for manufacturing mRNA encoding cystic fibrosis transmembrane conductance regulator, CFTR. The CFTR mRNA is delivered to the lung of a subject in need in a therapeutic composition for treating cystic fibrosis.

In certain embodiments, the present invention provides a method for producing a therapeutic composition comprising purified mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methyl malonic acidemia, or associated with any other metabolic disorder for which delivery to or treatment of the liver or a liver cell with enriched full-length mRNA provides therapeutic benefit.

In certain embodiments the present invention provides a method for producing a therapeutic composition comprising purified mRNA that encodes for a protein associated with a urea cycle disorder. In certain embodiments the present invention provides a method for producing a therapeutic composition comprising purified mRNA that encodes for omithine transcarbamylase (OTC) protein. In certain embodiments the present invention provides a method for producing a therapeutic composition comprising purified mRNA that encodes for arginosuccinate synthetase 1 protein. In certain embodiments the present invention provides a method for producing a therapeutic composition comprising purified mRNA that encodes for carbamoyl phosphate synthetase I protein. In certain embodiments the present invention provides a method for producing a therapeutic composition comprising purified mRNA that encodes for arginosuccinate lyase protein. In certain embodiments, the present invention provides a method for producing a therapeutic composition comprising purified mRNA that encodes for arginase protein.

In certain embodiments the present invention provides a method for producing a therapeutic composition comprising purified mRNA that encodes for a protein associated with a lysosomal storage disorder. In certain embodiments the present invention provides a method for producing a therapeutic composition comprising purified mRNA that encodes for alpha galactosidase protein. In certain embodiments the present invention provides a method for producing a therapeutic composition comprising purified mRNA that encodes for glucocerebrosidase protein. In certain embodiments the present invention provides a method for producing a therapeutic composition comprising purified mRNA that encodes for iduronate-2-sulfatase protein. In certain embodiments the present invention provides a method for producing a therapeutic composition comprising purified mRNA that encodes for iduronidase protein. In certain embodiments the present invention provides a method for producing a therapeutic composition comprising purified mRNA that encodes for N-acetyl-alpha-D-glucosaminidase protein. In certain embodiments the present invention provides a method for producing a therapeutic composition comprising purified mRNA that encodes for heparan N-sulfatase protein. In certain embodiments the present invention provides a method for producing a therapeutic composition comprising purified mRNA that encodes for galactosamine-6 sulfatase protein. In certain embodiments the present invention provides a method for producing a therapeutic composition comprising purified mRNA that encodes for beta-galactosidase protein. In certain embodiments the present invention provides a method for producing a therapeutic composition comprising purified mRNA that encodes for lysosomal lipase protein. In certain embodiments, the present invention provides a method for producing a therapeutic composition comprising purified mRNA that encodes for arylsulfatase B (N-acetylgalactosamine-4-sulfatase) protein. In certain embodiments, the present invention provides a method for producing a therapeutic composition comprising purified mRNA that encodes for transcription factor EB (TFEB).

In certain embodiments the present invention provides a method for producing a therapeutic composition comprising purified mRNA that encodes for a protein associated with a glycogen storage disorder. In certain embodiments the present invention provides a method for producing a therapeutic composition comprising purified mRNA that encodes for acid alpha-glucosidase protein. In certain embodiments the present invention provides a method for producing a therapeutic composition comprising purified mRNA that encodes for glucose-6-phosphatase (G6PC) protein. In certain embodiments the present invention provides a method for producing a therapeutic composition comprising purified mRNA that encodes for liver glycogen phosphorylase protein. In certain embodiments the present invention provides a method for producing a therapeutic composition comprising purified mRNA that encodes for muscle phosphoglycerate mutase protein. In certain embodiments the present invention provides a method for producing a therapeutic composition comprising purified mRNA that encodes for glycogen debranching enzyme.

In certain embodiments the present invention provides a method for producing a therapeutic composition comprising purified mRNA that encodes for a protein associated with amino acid metabolism. In certain embodiments the present invention provides a method for producing a therapeutic composition comprising purified mRNA that encodes for phenylalanine hydroxylase enzyme. In certain embodiments the present invention provides a method for producing a therapeutic composition comprising purified mRNA that encodes for glutaryl-CoA dehydrogenase enzyme. In certain embodiments the present invention provides a method for producing a therapeutic composition comprising purified mRNA that encodes for propionyl-CoA caboxylase enzyme. In certain embodiments, the present invention provides a method for producing a therapeutic composition comprising purified mRNA that encodes for oxalase alanine-glyoxylate aminotransferase enzyme.

In certain embodiments, the present invention provides a method for producing a therapeutic composition comprising purified mRNA that encodes for a protein associated with a lipid metabolism or fibrotic disorder. In certain embodiments the present invention provides a method for producing a therapeutic composition comprising purified mRNA that encodes for an mTOR inhibitor. In certain embodiments the present invention provides a method for producing a therapeutic composition comprising purified mRNA that encodes for ATPase phospholipid transporting 8B1 (ATP8B1) protein. In certain embodiments the present invention provides a method for producing a therapeutic composition comprising purified mRNA that encodes for one or more NF-kappa B inhibitors, such as one or more of I-kappa B alpha, interferon-related development regulator 1 (IFRD1), and Sirtuin 1 (SIRT1). In certain embodiments, the present invention provides a method for producing a therapeutic composition comprising purified mRNA that encodes for PPAR-gamma protein or an active variant.

In certain embodiments, the present invention provides a method for producing a therapeutic composition comprising purified mRNA that encodes for a protein associated with methyl malonic acidemia. For example, in certain embodiments the present invention provides a method for producing a therapeutic composition comprising purified mRNA that encodes for methyl malonyl CoA mutase protein. In certain embodiments, the present invention provides a method for producing a therapeutic composition comprising purified mRNA that encodes for methylmalonyl CoA epimerase protein.

In certain embodiments, the present invention provides a method for producing a therapeutic composition comprising purified mRNA for which delivery to or treatment of the liver can provide therapeutic benefit. In certain embodiments, the present invention provides a method for producing a therapeutic composition comprising purified mRNA that encodes for ATP7B protein, also known as Wilson disease protein. In certain embodiments, the present invention provides a method for producing a therapeutic composition comprising purified mRNA that encodes for porphobilinogen deaminase enzyme. In certain embodiments, the present invention provides a method for producing a therapeutic composition comprising purified mRNA that encodes for one or clotting enzymes, such as Factor VIII, Factor IX, Factor VII, and Factor X. In certain embodiments, the present invention provides a method for producing a therapeutic composition comprising purified mRNA that encodes for human hemochromatosis (HFE) protein.

In certain embodiments, the present invention provides a method for producing a therapeutic composition comprising purified mRNA that encodes a peptide or polypeptide for use in the delivery to or treatment of the cardiovascular conditions of a subject or a cardiovascular cell. In certain embodiments, the present invention provides a method for producing a therapeutic composition comprising purified mRNA that encodes for vascular endothelial growth factor A protein. In certain embodiments, the present invention provides a method for producing a therapeutic composition comprising purified mRNA that encodes for relaxin protein. In certain embodiments, the present invention provides a method for producing a therapeutic composition comprising purified mRNA that encodes for bone morphogenetic protein-9 protein. In certain embodiments, the present invention provides a method for producing a therapeutic composition comprising purified mRNA that encodes for bone morphogenetic protein-2 receptor protein.

In certain embodiments, the present invention provides a method for producing a therapeutic composition comprising purified mRNA that encodes a peptide or polypeptide for use in the delivery to or treatment of the muscle of a subject or a muscle cell. In certain embodiments, the present invention provides a method for producing a therapeutic composition comprising purified mRNA that encodes for dystrophin protein. In certain embodiments, the present invention provides a method for producing a therapeutic composition comprising purified mRNA that encodes for frataxin protein. In certain embodiments, the present invention provides a method for producing a therapeutic composition comprising purified mRNA that encodes a peptide or polypeptide for use in the delivery to or treatment of the cardiac muscle of a subject or a cardiac muscle cell. In certain embodiments, the present invention provides a method for producing a therapeutic composition comprising purified mRNA that encodes for a protein that modulates one or both of a potassium channel and a sodium channel in muscle tissue or in a muscle cell. In certain embodiments the present invention provides a method for producing a therapeutic composition comprising purified mRNA that encodes for a protein that modulates a Kv7.1 channel in muscle tissue or in a muscle cell. In certain embodiments, the present invention provides a method for producing a therapeutic composition comprising purified mRNA that encodes for a protein that modulates a Nav1.5 channel in muscle tissue or in a muscle cell.

In certain embodiments, the present invention provides a method for producing a therapeutic composition comprising purified mRNA that encodes a peptide or polypeptide for use in the delivery to or treatment of the nervous system of a subject or a nervous system cell. For example, in certain embodiments the present invention provides a method for producing a therapeutic composition comprising purified mRNA that encodes for survival motor neuron 1 protein. For example, in certain embodiments the present invention provides a method for producing a therapeutic composition comprising purified mRNA that encodes for survival motor neuron 2 protein. In certain embodiments, the present invention provides a method for producing a therapeutic composition comprising purified mRNA that encodes for frataxin protein. In certain embodiments, the present invention provides a method for producing a therapeutic composition comprising purified mRNA that encodes for ATP binding cassette subfamily D member 1 (ABCD1) protein. In certain embodiments, the present invention provides a method for producing a therapeutic composition comprising purified mRNA that encodes for CLN3 protein.

In certain embodiments, the present invention provides a method for producing a therapeutic composition comprising purified mRNA that encodes a peptide or polypeptide for use in the delivery to or treatment of the blood or bone marrow of a subject or a blood or bone marrow cell. In certain embodiments, the present invention provides a method for producing a therapeutic composition comprising purified mRNA that encodes for beta globin protein. In certain embodiments, the present invention provides a method for producing a therapeutic composition comprising purified mRNA that encodes for Bruton's tyrosine kinase protein. In certain embodiments, the present invention provides a method for producing a therapeutic composition comprising purified mRNA that encodes for one or clotting enzymes, such as Factor VIII, Factor IX, Factor VII, and Factor X.

In certain embodiments, the present invention provides a method for producing a therapeutic composition comprising purified mRNA that encodes a peptide or polypeptide for use in the delivery to or treatment of the kidney of a subject or a kidney cell. In certain embodiments, the present invention provides a method for producing a therapeutic composition comprising purified mRNA that encodes for collagen type IV alpha 5 chain (COL4A5) protein.

In certain embodiments, the present invention provides a method for producing a therapeutic composition comprising purified mRNA that encodes a peptide or polypeptide for use in the delivery to or treatment of the eye of a subject or an eye cell. In certain embodiments, the present invention provides a method for producing a therapeutic composition comprising purified mRNA that encodes for ATP-binding cassette sub-family A member 4 (ABCA4) protein. In certain embodiments, the present invention provides a method for producing a therapeutic composition comprising purified mRNA that encodes for retinoschisin protein. In certain embodiments, the present invention provides a method for producing a therapeutic composition comprising purified mRNA that encodes for retinal pigment epithelium-specific 65 kDa (RPE65) protein. In certain embodiments, the present invention provides a method for producing a therapeutic composition comprising purified mRNA that encodes for centrosomal protein of 290 kDa (CEP290).

In certain embodiments, the present invention provides a method for producing a therapeutic composition comprising purified mRNA that encodes a peptide or polypeptide for use in the delivery of or treatment with a vaccine for a subject or a cell of a subject. For example, in certain embodiments the present invention provides a method for producing a therapeutic composition comprising purified mRNA that encodes for an antigen from an infectious agent, such as a virus. In certain embodiments, the present invention provides a method for producing a therapeutic composition comprising purified mRNA that encodes for an antigen from influenza virus. In certain embodiments, the present invention provides a method for producing a therapeutic composition comprising purified mRNA that encodes for an antigen from respiratory syncytial virus. In certain embodiments, the present invention provides a method for producing a therapeutic composition comprising purified mRNA that encodes for an antigen from rabies virus. In certain embodiments, the present invention provides a method for producing a therapeutic composition comprising purified mRNA that encodes for an antigen from cytomegalovirus. In certain embodiments, the present invention provides a method for producing a therapeutic composition comprising purified mRNA that encodes for an antigen from rotavirus. In certain embodiments, the present invention provides a method for producing a therapeutic composition comprising purified mRNA that encodes for an antigen from a hepatitis virus, such as hepatitis A virus, hepatitis B virus, or hepatitis C virus. In certain embodiments, the present invention provides a method for producing a therapeutic composition comprising purified mRNA that encodes for an antigen from human papillomavirus. In certain embodiments, the present invention provides a method for producing a therapeutic composition comprising purified mRNA that encodes for an antigen from a herpes simplex virus, such as herpes simplex virus 1 or herpes simplex virus 2. In certain embodiments, the present invention provides a method for producing a therapeutic composition comprising purified mRNA that encodes for an antigen from a human immunodeficiency virus, such as human immunodeficiency virus type 1 or human immunodeficiency virus type 2. In certain embodiments, the present invention provides a method for producing a therapeutic composition comprising purified mRNA that encodes for an antigen from a human metapneumovirus. In certain embodiments, the present invention provides a method for producing a therapeutic composition comprising purified mRNA that encodes for an antigen from a human parainfluenza virus, such as human parainfluenza virus type 1, human parainfluenza virus type 2, or human parainfluenza virus type 3. In certain embodiments, the present invention provides a method for producing a therapeutic composition comprising purified mRNA that encodes for an antigen from malaria virus. In certain embodiments, the present invention provides a method for producing a therapeutic composition comprising purified mRNA that encodes for an antigen from zika virus. In certain embodiments, the present invention provides a method for producing a therapeutic composition comprising purified mRNA that encodes for an antigen from chikungunya virus.

In certain embodiments, the present invention provides a method for producing a therapeutic composition comprising purified mRNA that encodes for an antigen associated with a cancer of a subject or identified from a cancer cell of a subject. In certain embodiments, the present invention provides a method for producing a therapeutic composition comprising purified mRNA that encodes for an antigen determined from a subject's own cancer cell, i.e., to provide a personalized cancer vaccine. In certain embodiments, the present invention provides a method for producing a therapeutic composition comprising purified mRNA that encodes for an antigen expressed from a mutant KRAS gene.

In certain embodiments, the present invention provides a method for producing a therapeutic composition comprising purified mRNA that encodes for an antibody. In certain embodiments, the antibody can be a bi-specific antibody. In certain embodiments, the antibody can be part of a fusion protein. In some embodiments, two separate mRNA-LNPs in step (b) of the process comprise mRNA encoding a light chain and heavy chain of an antibody. In some embodiments, the mRNA-LNP composition of the invention may comprise a combination of non-identical LNPs comprising different lipid composition, and encapsulating mRNA encoding a light chain or a heavy chain of an antibody. In certain embodiments, the present invention provides a method for producing a therapeutic composition comprising purified mRNA that encodes for an antibody to OX40. In certain embodiments, the present invention provides a method for producing a therapeutic composition comprising purified mRNA that encodes for an antibody to VEGF. In certain embodiments, the present invention provides a method for producing a therapeutic composition comprising purified mRNA that encodes for an antibody to tissue necrosis factor alpha. In certain embodiments the present invention provides a method for producing a therapeutic composition comprising purified mRNA that encodes for an antibody to CD3. In certain embodiments the present invention provides a method for producing a therapeutic composition comprising purified mRNA that encodes for an antibody to CD19.

In certain embodiments, the present invention provides a method for producing a therapeutic composition comprising purified mRNA that encodes for an immunomodulator. In certain embodiments, the present invention provides a method for producing a therapeutic composition comprising purified mRNA that encodes for Interleukin 12. In certain embodiments, the present invention provides a method for producing a therapeutic composition comprising purified mRNA that encodes for Interleukin 23. In certain embodiments, the present invention provides a method for producing a therapeutic composition comprising purified mRNA that encodes for Interleukin 36 gamma. In certain embodiments, the present invention provides a method for producing a therapeutic composition comprising purified mRNA that encodes for a constitutively active variant of one or more stimulator of interferon genes (STING) proteins.

In certain embodiments, the present invention provides a method for producing a therapeutic composition comprising purified mRNA that encodes for an endonuclease. In certain embodiments, the present invention provides a method for producing a therapeutic composition comprising purified mRNA that encodes for an RNA-guided DNA endonuclease protein, such as Cas 9 protein. In certain embodiments, the present invention provides a method for producing a therapeutic composition comprising purified mRNA that encodes for a meganuclease protein. In certain embodiments, the present invention provides a method for producing a therapeutic composition comprising purified mRNA that encodes for a transcription activator-like effector nuclease protein. In certain embodiments, the present invention provides a method for producing a therapeutic composition comprising purified mRNA that encodes for a zinc finger nuclease protein.

In certain embodiments, the present invention provides a method for producing a therapeutic composition comprising purified mRNA that encodes for treating an ocular disease. In some embodiments, the method is used for producing a therapeutic composition comprising purified mRNA encoding retinoschisin.

EXAMPLES

While certain compounds, compositions and methods of the present invention have been described with specificity in accordance with certain embodiments, the following examples serve only to illustrate the invention and are not intended to limit the same. While certain compounds, compositions and methods of the present invention have been described with specificity in accordance with certain embodiments, the following examples serve only to illustrate the invention and are not intended to limit the same.

The mRNA-LNP test articles described in the following examples, unless otherwise specified, contain mRNA encapsulated in a multi-component lipid mixture of varying ratios employing one or more cationic lipids, one or more helper lipids (e.g., non-cationic lipids such as DEPE or DOPE), one or more PEGylated lipids, and optionally one or more sterols, such as cholesterol designed to encapsulate mRNA.

Example 1. Preparation of mRNA

In Vitro Transcription of mRNA

Unless otherwise described, mRNA was synthesized via in vitro transcription (IVT) using either T7 polymerase or SP6 polymerase. Briefly, in the SP6 polymerase IVT reaction, for each gram of mRNA transcribed, a reaction containing 20 mg of a linearized double stranded DNA plasmid with an RNA polymerase specific promoter, SP6 RNA polymerase, RNase inhibitor, pyrophosphatase, 5 mM NTPs, 10 mM DTT and a reaction buffer (10×—250 mM Tris-HCl, pH 7.5, 20 mM spirmidine, 50 mM NaCl) was prepared with RNase free water then incubated at 37 C for 60 min. The reaction was then quenched by the addition of DNase I and a DNase I buffer (10×—100 mM Tris-HCl, 5 mM $MgCl_2$ and 25 mM $CaCl_2$), pH 7.6) to facilitate digestion of the double stranded DNA template in preparation for purification.

5' Capping of mRNA

Unless otherwise described the IVT transcribed mRNA was capped on its 5' end either by including cap structures as part of the IVT reaction or in a subsequent enzymatic step. For capping as part of the IVT reaction, a cap analog can be incorporated as the first "base" in the nascent RNA strand. The cap analog may be Cap 0, Cap1, Cap 2, $^{m6}A_m$, or unnatural caps. Alternatively, uncapped and purified in vitro transcribed (IVT) mRNA can be modified enzymatically following IVT to include a cap, e.g., by the addition of a 5' $N^7$-methylguanylate Cap 0 structure using guanylate transferase and the addition of a methyl group at the 2' O position of the penultimate nucleotide resulting in a Cap 1 structure using 2' O-methyltransferase as described by Fechter, P.; Brownlee, G. G. "Recognition of mRNA cap structures by viral and cellular proteins" *J. Gen. Virology* 2005, 86, 1239-1249.

3' Tailing of mRNA

Unless otherwise described, the IVT transcribed mRNA was tailed on its 3' end either by including a tail template in the linearized plasmid, which tails the mRNA as part of the IVT reaction, or in a subsequent enzymatic step. For tailing as part of the IVT reaction, incorporation of a poly-T or similar tailing feature into the pDNA template is performed such that the polyA tail or similar appropriate tail is formed on the mRNA as part of the IVT process. Alternatively, a poly-A tail can be added to the 3' end of the IVT-produced mRNA enzymatically following the IVT reaction, e.g., using poly-A polymerase.

Example 2. Preparation of Lipid Nanoparticles (LNPs) and Encapsulation of mRNA LNP preparation and encapsulation of mRNA in LNPs comprising Compound 3 as the cationic lipid were performed according to Process B. Process B is further described in U.S. Published Patent Application No. US2018153822, which is herein incorporated by reference for all purposes. As noted above, the LNP preparations were multi-component lipid mixtures including one or more cationic lipids, one or more helper lipids (e.g., non-cationic lipids such as DEPE or DOPE), one or more PEGylated lipids, and one or more sterols, such as cholesterol designed to encapsulate mRNA obtained as described in Example 1.

As used herein, Process A refers to a conventional process in which LNPs are formed from a multi-component mixture of lipids and the mRNA is encapsulated in those forming LNPs in a single step.

Process B refers to a process of encapsulating mRNA by mixing pre-formed LNPs with mRNA. The pre-formed LNPs were first prepared by instantaneously mixing a multi-component lipid mixture dissolved in a solvent, such as ethanol with a citrate buffer, in the absence of mRNA. The mixing of the two streams resulted in the formation of empty lipid nanoparticles, which was a self-assembly process. The resultant formulation provided empty lipid nanoparticles in citrate buffer containing alcohol, which was buffer exchanged (e.g., by tangential flow filtration (TFF)) to provide empty lipid nanoparticles in a 10% weight/volume trehalose solution buffer. Then, the empty lipid nanoparticles and mRNA in an aqueous solution were mixed to form mRNA encapsulated within the lipid nanoparticles.

Specifically, to prepare empty lipid nanoparticles, either DEPE or DOPE was used as the helper lipid, together with Compound 3 as the cationic lipid, DMG-PEG2K as the PEG-modified lipid and cholesterol at the ratios described in Table 2-1.

TABLE 2-1

Lipid Nanoparticle Formation with DEPE versus DOPE

| Test Article | mRNA | LNP Helper Lipid | LNP Lipid Molar Ratio (Compound 3:DMG-PEG2K:Cholesterol:Helper Lipid) | N/P ratio | Particle size (nm) | Polydispersity Index (PDI) | % Encapsulation |
|---|---|---|---|---|---|---|---|
| 1 | EPO | DOPE | 40:3:25:32 | 4 | n/a | n/a | n/a |
| 2 | EPO | DEPE | 40:3:25:32 | 4 | 152 | 0.14 | 68.7 |

Surprisingly, it was found that these multi-component lipid mixtures with Compound 3 as the cationic lipid could not be formulated using DOPE as the non-cationic helper lipid but formed stable liposomes when DEPE was used as the non-cationic helper lipid instead of DOPE.

Example 3. Enhanced In Vivo Production of mRNA in an LNP with DEPE

This example illustrates the unexpected increase in potency of LNP encapsulated mRNA using an LNP that includes DEPE as a helper lipid.

mRNA encoding EPO was synthesized as described in Example 1. Using Process B as described in Example 2, the mRNA was encapsulated into LNPs which comprised different helper lipids but which were otherwise the same (see Table 3-1 below). Specifically, each mRNA-encapsulated LNP included a different helper lipid but the same cationic lipid (Compound 1), the same PEG-modified lipid (DMG-PEG2K), the same sterol compound (cholesterol), the same molar ratios of those lipids, the same mRNA (EPO mRNA), the same N/P ratio=4 (i.e., the molar ratio of cationic lipid to mRNA), the same mRNA concentration (0.2 mg/mL) and were prepared according to the same process (Process B). The characteristics of the resulting mRNA-LNPs are provided in Table 3-1.

TABLE 3-1

Characteristics of EPO mRNA-LNP

| Test Article | mRNA | LNP Helper Lipid | LNP Lipid Molar Ratio (Compound 1:DMG-PEG2K:Cholesterol:Helper Lipid) | N/P ratio | Conc. mg/mL | Particle size (nm) | Polydispersity Index (PDI) | % Encapsulation |
|---|---|---|---|---|---|---|---|---|
| 1 | EPO | DOPE | 40:3:25:32 | 4 | 0.2 | 112 | 0.144 | 92.5 |
| 2 | EPO | DLOPE | 40:3:25:32 | 4 | 0.2 | 107 | 0.146 | 91.3 |
| 3 | EPO | POPE | 40:3:25:32 | 4 | 0.2 | 121 | 0.145 | 96.5 |
| 4 | EPO | DEPE | 40:3:25:32 | 4 | 0.2 | 120 | 0.129 | 98.4 |

-

Each of the four test articles comprising mRNA encapsulated in an LNP with a different helper lipid (1-4 in Table 3-1) was administered to mice intravenously by tail vein injection (n=5, CD-1 mice 6-8 weeks of age) at a dose of 1 mg/kg mRNA in a dose volume of 5 mL/kg. At 6 hours post-dose administration, interim whole blood was collected by tail snip. At 24 hours post-dose administration, all animals were euthanized followed by thoracotomy and terminal blood collection. Human erythropoietin (hEPO) levels in sera samples were determined by ELISA kit (R&D system Cat #DEP00) according to the manufacturer instruction. In addition, sera ALT and AST levels were measured by ELISA according to standard techniques. The EPO protein expression and ALT/AST results are provided in Table 3-2 and graphically depicted in FIG. 1 and in FIG. 2, respectively.

TABLE 3-2

In vivo Experimental Plan for Example 3

| Test Article | LNP Helper Lipid | Protein Expression from mRNA at 6 hours post-dose ug/mL (st.dev.) | Protein Expression from mRNA at 24 hours post-dose ug/mL (st.dev.) | ALT at 24 hours post-dose U/L (st.dev) | AST at 24 hours post-dose U/L (st.dev) |
|---|---|---|---|---|---|
| 1 | DOPE | 8.30 (3.45) | 4.44 (2.09) | 41.9 (4.6) | 87.0 (8.9) |
| 2 | DLOPE | 7.92 (4.59) | 2.61 (0.72) | 31.9 (8.3) | 93.4 (12.3) |
| 3 | POPE | 8.65 (3.40) | 4.45 (1.56) | 38.8 (8.2) | 108.3 (5.4) |
| 4 | DEPE | 25.23 (10.45) | 13.75 (7.95) | 40.3 (5.6) | 95.1 (8.8) |

As shown in Table 3-2 and in FIG. 1, the mRNA LNPs comprising DEPE as the helper lipid provided remarkably higher in vivo protein expression as compared to protein expression from mRNA LNPs comprising other helper lipids but that were otherwise the same. Specifically, at six hours post-dose administration, the mRNA LNPs comprising DEPE provided an in vivo protein expression that was enhanced to more than 100%, i.e., to more than two times higher, the protein expression from mRNA LNPs comprising a helper lipid other than DEPE, e.g., DOPE, DLOPE, or POPE, at the same timepoint. Similarly, at 24 hours post-dose administration, the mRNA LNPs comprising DEPE provided an in vivo protein expression that was enhanced to more than 100%, i.e., to more than two times higher, the protein expression from mRNA LNPs comprising a helper lipid other than DEPE, e.g., DOPE, DLOPE, or POPE, at the same time point.

Figure 2:
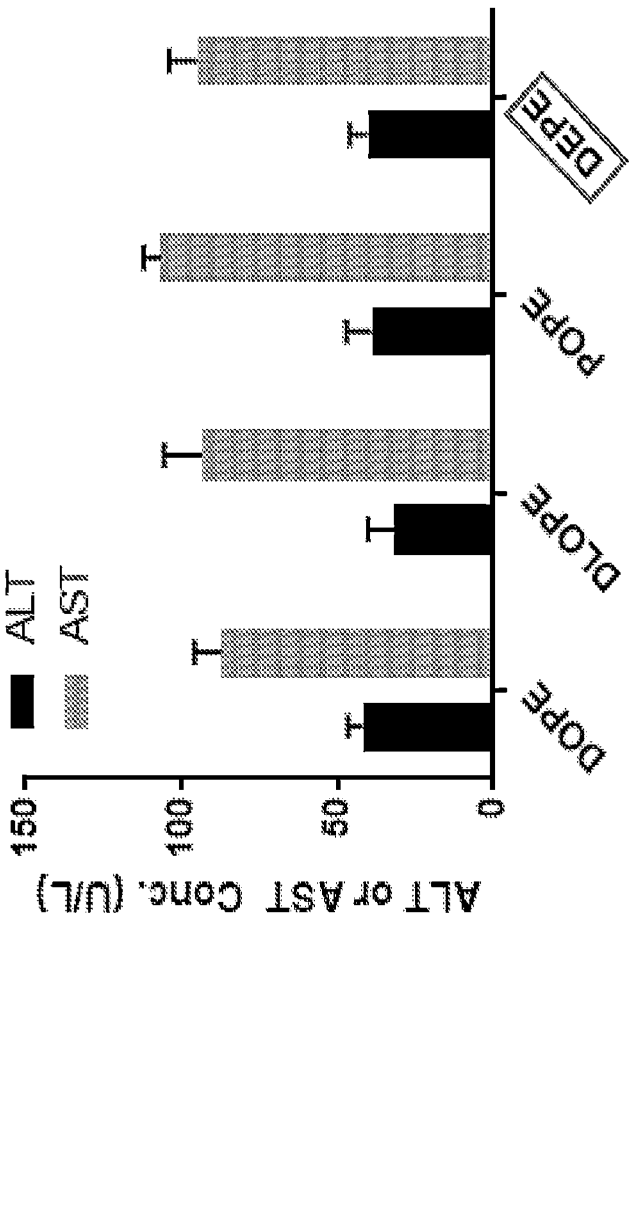
FIG. 2 depicts an exemplary graphical representation of post-dose level of sera ALT and AST for mRNA LNPs comprising DEPE and other helper lipids.

Moreover, as also shown in Table 3-2 and in FIG. 2, the ALT and AST levels at 24 hours post-dose administration were substantially similar for all mRNA LNPs regardless of helper lipid, indicating that mRNA LNPs comprising DEPE as helper lipid have similar safety and tolerability to mRNA LNPs comprising a helper lipid other than DEPE, e.g., DOPE, DLOPE, or POPE, while at the same time being remarkably more potent.

Example 4. Preparation of Lipid Nanoparticles (LNPs) Using DEPE or DOPE as Helper Lipids This example illustrates that using DEPE as a helper lipid in mRNA-encapsulating lipid nanoparticle (mRNA-LNP) formulations can provide increased protein expression from the mRNA in vivo by up to more than two-fold relative to conventional liposomes comprising (DOPE) as a helper lipid. It was also observed that the mRNA-LNPs with DEPE as a helper lipid provided increased encapsulation efficiency as compared to the same mRNA-LNPs with DOPE as a helper lipid. Notably, this enhanced expression and this enhanced encapsulation efficiency was observed across a wide variety of mRNA-LNPs comprising different cationic lipids.

In these studies, mRNA encoding OTC was encapsulated in LNPs comprising DEPE or DOPE as helper lipids and various cationic lipids listed in Table 4. Each cationic lipid described in Table 4 included four alkyl chains of $C_{10}$, $C_{12}$, $C_{14}$, or $C_{16}$ in length, as denoted by the ending two digit number in the description of each lipid. The molar ratio of cationic lipid:DMG-PEG2K:Cholesterol:Helper Lipid was about 40:3:25:32. For the in vivo portion of the studies, 1 mg/kg of each formulated mRNA-LNP was delivered to mice via tail vein injection. At 24 hours mice were sacrificed and the in vivo expression of mRNA encoding OTC was assessed from liver homogenate from each mouse. The mean protein expression is provided in the table below.

TABLE 4

Protein Expression and Encapsulation Efficiency of LNPs with DEPE versus DOPE as a Helper Lipid

| Cationic Lipid | Protein Expression (ng/mL) | | Encapsulation % | |
|---|---|---|---|---|
| | DOPE | DEPE | DOPE | DEPE |
| cDD-TE-4-E10 | 86.44 | 516.96 | 87.49 | 95.53 |
| cDD-TE-4-E12 | 96.39 | 764.91 | 85.73 | 91.6 |
| cDD-TE-4-E14 | 81.85 | 69.05 | 71.84 | 70.9 |
| cHse-E-2-E10 | 128.892 | 100.37 | 82 | 96.74 |
| cHse-E-2-E12 | 226.887 | 248.68 | 81 | 99.33 |
| cHse-E-3-E10 | 1706.15 | 4462.86 | 84.8 | 96.9 |
| cHse-E-3-E12 | 1411.27 | 3190.32 | 85.11 | 97.52 |
| cHse-E-3-E14 | Aggregates | 1617.88 | Aggregates | 90.6 |
| cHse-E-3-E16 | Low Encap | 135.68 | Low Encap | 67.4 |

Table 4 demonstrates that encapsulation efficiency was greater when DEPE was used as a helper lipid, as compared to DOPE. In addition, it was surprising to observe that multi-component lipid mixtures with certain of the lipidoids as the cationic lipids could not be even formulated using DOPE but formed stable liposomes when DEPE was used as the helper lipid. Table 4 also demonstrates that the mRNA LNPs comprising DEPE as the helper lipid showed remarkably higher in vivo protein expression as compared to protein expression from mRNA LNPs comprising DOPE helper lipid but that were otherwise the same. This was true when various cationic lipids were used in LNPs.

Example 5. Enhanced In Vivo Protein Expression by Using DEPE as Helper Lipid as Compared to Other Helper Lipids This example illustrates that using DEPE as a helper lipid in an mRNA-encapsulating lipid nanoparticle (mRNA-LNP) can increase expression of mRNA in vivo relative to lipid nanoparticles that use other types of helper lipids, across a variety of encapsulation processed used to preparing the mRNA-LNPs.

In these studies, mRNA encoding OTC was encapsulated in LNPs (N/P=4) comprising DMG-PEG-2000 as PEG-modified lipid, cDD-TE-4-E12 as a cationic lipid, cholesterol, and one of several different helper lipids, including DEPE, at molar lipid ratios as shown in Table 5-1, Table 5-2, Table 5-3 and Table 5-4. Each mRNA-LNP formulation was prepared by using one of four different encapsulation processes: conventional process, for formulations described in Table 5-1, Remix process for formulations described in Table 5-2, Step-Up Remix process for formulations described in Table 5-3, or Step-Down Remix process for formulations described in Table 5-4. mRNA-LNPs were assessed for LNP size, polydispersity and percent encapsulation, with the results for each presented in the tables below. For the in vivo portion of the studies, 1 mg/kg of each formulated mRNA-LNP was delivered to mice (n=5) via tail vein injection. At 24 hours mice were sacrificed and the in vivo expression of mRNA encoding OTC was assessed from liver homogenate from each mouse. The mean protein expression is provided in the tables below.

TABLE 5-1 mRNA-LNPs with Different Helper Lipids Prepared via Conventional EncapsulationHelper

| Lipid | Lipid Ratios (PEG:cat:chol:help) | Size (nm) | PdI | Encapsulation (%) | Protein Expression (ng/mg) Mean | Protein Expression (ng/mg) SD |
|---|---|---|---|---|---|---|
| DEPE | 3:40:25:32 | 78 | 0.17 | 98 | 1454 | 755 |
| DEPE | 2:40:25:33 | 76 | 0.15 | 100 | 1634 | 522 |
| DOPE | 1.5:40:26.5:32 | 80 | 0.09 | 99 | 618 | 440 |
| PE20:4 | 3:40:25:32 | 81 | 0.22 | 92 | 0 | 0 |

TABLE 5-2 mRNA-LNPs with Different Helper Lipids Prepared via Remix Encapsulation

| Helper Lipid | Lipid Ratios (PEG:cat:chol:help) | Size (nm) | PdI | Encapsulation (%) | Protein Expression (ng/mg) Mean | Protein Expression (ng/mg) SD |
|---|---|---|---|---|---|---|
| DEPE | 3:40:25:32 | 120 | 0.17 | 92 | 765 | 290 |
| DOPE | 3:40:25:32 | 111 | 0.19 | 86 | 96 | 41 |
| 16:0-18:2 PE | 3:40:25:32 | 115 | 0.15 | 64 | 0 | 0 |
| 16:0-20:4 PE | 3:40:25:32 | 109 | 0.14 | 68 | 0 | 0 |
| 16:0-22:6 PE | 3:40:25:32 | 95 | 0.13 | 79 | 0 | 0 |
| DOCP | 3:40:25:32 | 80 | 0.194 | 83 | 0 | 0 |
| DOCPe | 3:40:25:32 | 110 | 0.24 | 65 | 0 | 0 |
| PE20:4 | 3:40:25:32 | 105 | 0.16 | 97 | 0 | 0 |

TABLE 5-3 mRNA-LNPs with Different Helper Lipids Prepared via Step-Up Remix Encapsulation

| Helper Lipid | Lipid Ratios (PEG:cat:chol:help) | Size (nm) | PdI | Encapsulation (%) | Protein Expression (ng/mg) Mean | Protein Expression (ng/mg) SD |
|---|---|---|---|---|---|---|
| DEPE | 3:40:25:32 | 124 | 0.12 | 96 | 1258 | 342 |
| DOPE | 3:40:27:30 | 138 | 0.18 | 93 | 579 | 302 |
| 18:0-18:2 PE | 3:40:25:32 | 115 | 0.12 | 87 | 0 | 0 |
| 18:0-20:4 PE | 3:40:25:32 | 87 | 0.12 | 79 | 0 | 0 |

TABLE 5-4 mRNA-LNPs with Different Helper Lipids Prepared via Step-Down Remix Encapsulation

| Helper Lipid | Lipid Ratios (PEG:cat:chol:help) | Size (nm) | PdI | Encapsulation (%) | Protein Expression (ng/mg) Mean | Protein Expression (ng/mg) SD |
|---|---|---|---|---|---|---|
| DEPE | 3:40:25:32 | 118 | 0.10 | 96 | 1247 | 223 |
| DOPE | 3:40:27:30 | 124 | 0.16 | 90 | 527 | 288 |
| DOCPe | 3:40:25:32 | 115 | 0.24 | 64 | 0 | 0 |

Table 5-1, Table 5-2, Table 5-3 and Table 5-4 each show levels of protein expression after 24 hours by the mRNA encapsulated in LNPs and delivered to the groups of mice. As shown, only LNPs prepared with the helper lipids DOPE or DEPE provided potency in terms of protein expression across the different encapsulation processes. Notably, in vivo protein expression was highest when DEPE was used a helper lipid to prepare the LNPs, regardless of the encapsulation process used to prepare the mRNA-LNPs.

As one skilled in the art can appreciate, this significantly increased potency but comparable safety and efficacy of mRNA LNPs comprising DEPE as helper lipid offers significant advantages for delivery of mRNA as a therapeutic.

EQUIVALENTS

Those skilled in the art will recognize, or be able to ascertain, using no more than routine experimentation, many equivalents to the specific embodiments of the invention described herein. The scope of the present invention is not intended to be limited to the above Description, but rather is as set forth in the following claims:

We claim:

1. A lipid nanoparticle for the delivery of mRNA to a subject in need thereof, the lipid nanoparticle comprising one or more cationic lipids at a concentration between 30 molar percent and 60 molar percent, one or more PEG-modified lipids at a concentration between 1 molar percent and 15 molar percent, one or more helper lipids comprising 1,2-Dierucoyl-sn-glycero-3-phosphoethanolamine (DEPE), and wherein the DEPE is present at a concentration between 25 molar percent and 35 molar percent, and one or more sterols at a concentration between 20 molar percent and 30 molar percent, wherein the molar percents are of total lipids in the lipid nanoparticle and wherein the lipid nanoparticle encapsulates the mRNA.

2. The lipid nanoparticle of claim 1, wherein the one or more cationic lipids are or comprise a cationic lipid that comprises one to four alkyl chains, each of $C_{10}$-$C_{16}$ in length.

3. The lipid nanoparticle of claim 1, wherein the one or more cationic lipids are or comprise a cationic lipid of the following formula:

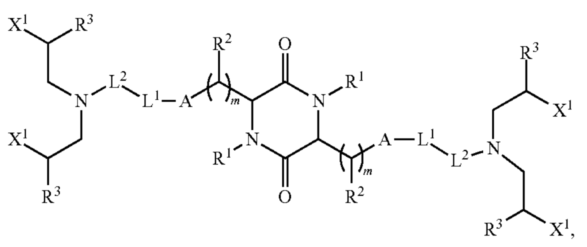

or a pharmaceutically acceptable salt thereof; wherein each of $R^1$ and $R^2$ is independently H or $C_1$-$C_6$ aliphatic;

each m is independently an integer having a value of 1 to 4;

each A is independently a covalent bond or arylene;

each $L^1$ is independently an ester, thioester, disulfide, or anhydride group;

each $L^2$ is independently $C_2$-$C_{10}$ aliphatic;

each $X^1$ is independently H or OH; and each $R^3$ is independently $C_6$-$C_{20}$ aliphatic.

4. The lipid nanoparticle of claim 1, wherein the one or more PEG-modified lipids comprise a poly (ethylene) glycol chain of up to 5 kDa covalently attached to a lipid with alkyl chain(s) of $C_6$-$C_{20}$ in length.

5. The lipid nanoparticle of claim 1, wherein the mRNA encodes a therapeutic protein or peptide.

6. A pharmaceutical composition comprising a plurality of the lipid nanoparticle of claim 1, wherein greater than 70% of the lipid nanoparticles in the composition have a size ranging from 75 nm to 150 nm.

7. The lipid nanoparticle of claim 1, wherein the one or more cationic lipids are a lipidoid comprising four aliphatic chains.

8. The lipid nanoparticle of claim 1, wherein the mRNA encodes an antigen.

9. The lipid nanoparticle of claim 1, wherein the mRNA encodes an antibody light chain or an antibody heavy chain.

10. The lipid nanoparticle of claim 1, wherein the mRNA encodes a polypeptide absent or deficient in the subject.

11. The lipid nanoparticle of claim 3, wherein each $R^3$ is independently $C_8$-$C_{16}$ aliphatic.

12. The lipid nanoparticle of claim 1, wherein the one or more sterols comprise a cholesterol or PEGylated cholesterol, or a combination thereof.

13. The lipid nanoparticle of claim 1, wherein the one or more cationic lipids are present at a concentration of about 40 molar percent, the one or more PEG-modified lipids are present at a concentration of about 3 molar percent, the DEPE is present at a concentration of about 32 molar percent, and the one or more sterols are present at a concentration of about 25 molar percent, wherein the molar percents are of total lipids in the lipid nanoparticle.

14. The lipid nanoparticle of claim 13, wherein the one or more sterols comprise a cholesterol.

15. The lipid nanoparticle of claim 1, wherein the one or more cationic lipids are or comprise Compound 1:

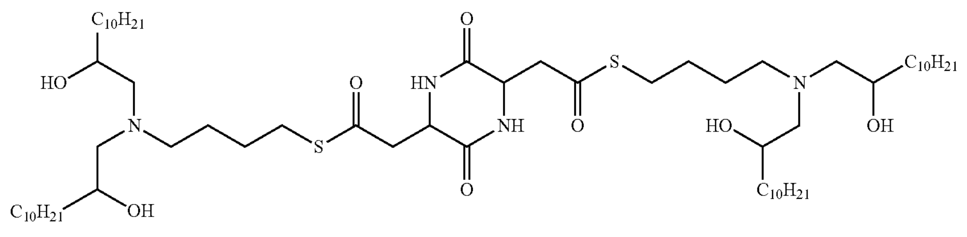

or a pharmaceutically acceptable salt thereof.

16. The lipid nanoparticle of claim 1, wherein the one or more cationic lipids are or comprise cKK-E12 or a pharmaceutically acceptable salt thereof.

17. The lipid nanoparticle of claim 1, wherein the one or more cationic lipids are or comprise imidazole cholesterol ester or a pharmaceutically acceptable salt thereof.

18. The lipid nanoparticle of claim 1, wherein the one or more PEG-modified lipids are or comprise 1,2-dimyristoyl-rac-glycero-3-methoxypolyethylene glycol-2000.

* * * * *